(12) United States Patent
Silver et al.

(10) Patent No.: US 7,166,087 B2
(45) Date of Patent: Jan. 23, 2007

(54) BREASTSHIELD WITH MULTI-PRESSURE AND EXPANSIBLE CHAMBER CONSTRUCTION, RELATED BREASTPUMP AND METHOD

(75) Inventors: Brian H. Silver, Cary, IL (US); Russ Schweizer, Crystal Lake, IL (US)

(73) Assignee: Medela Holding AG, Baar (CH)

( * ) Notice: Subject to any disclaimer, the term of this patent is extended or adjusted under 35 U.S.C. 154(b) by 70 days.

(21) Appl. No.: 10/619,834

(22) Filed: Jul. 15, 2003

(65) Prior Publication Data

US 2004/0015127 A1 Jan. 22, 2004

Related U.S. Application Data

(62) Division of application No. 09/888,322, filed on Jun. 22, 2001, now Pat. No. 6,663,587.

(51) Int. Cl.
*A61M 1/06* (2006.01)
(52) U.S. Cl. ........................................... 604/74
(58) Field of Classification Search ............. 604/73–76
See application file for complete search history.

(56) References Cited

U.S. PATENT DOCUMENTS

| | | | |
|---|---|---|---|
| 956,325 A | 4/1910 | Fey | |
| 1,032,518 A | 7/1912 | Thieringer | |
| 1,721,739 A | 7/1929 | Kennedy | |
| 2,542,505 A | 2/1951 | Gascoigne | 128/281 |
| 3,822,703 A | 7/1974 | Davisson | 128/281 |

(Continued)

FOREIGN PATENT DOCUMENTS

AU 121942 8/1946

(Continued)

OTHER PUBLICATIONS

Circle Caring, Ameda Egnell, Jun. 24, 1991.

(Continued)

*Primary Examiner*—Catherine S. Williams
(74) *Attorney, Agent, or Firm*—Baniak Pine & Gannon

(57) ABSTRACT

Inner and outer shield parts of a breastshield are joined to form an enclosure defining a pressurizable chamber. The inner shield part has at least a portion thereof movable relative to the outer shield part when the chamber is subject to a negative or a positive pressure. A first pressure port is in communication respectively with the chamber for connection with a fluid pressure source of a first pressure. A second pressure port is in communication with the interior for connection with a pressure source of a second pressure. The breastshield is thus capable of being subjected to two different pressures, such as a positive pressure to move (expand) the chamber into the interior, so as to compress or massage the nipple/breast, and a negative pressure in the interior to draw the nipple/breast further therein for the expression of milk. The pressures can be independently controlled, and may furthermore alternate being negative and positive through the same pressure port. In one embodiment, an enclosure defines first and second chambers. The chambers are separate from each other and independently pressurizable. A greater plurality of chambers is furthermore contemplated. The invention takes the form of a variety of different embodiments of breastshields and breastpumps for breastmilk pumping having sundry novel attributes and advantages.

3 Claims, 18 Drawing Sheets

U.S. PATENT DOCUMENTS

| | | | |
|---|---|---|---|
| 4,249,481 A * | 2/1981 | Adams | 119/14.02 |
| 4,263,912 A | 4/1981 | Adams | 128/281 |
| 4,323,067 A | 4/1982 | Adams | 128/281 |
| 4,680,028 A | 7/1987 | Stuart | 604/74 |
| 4,772,262 A | 9/1988 | Grant et al. | 604/74 |
| 4,794,915 A | 1/1989 | Larsson | 128/64 |
| 4,799,922 A | 1/1989 | Beer et al. | 604/74 |
| 4,857,051 A | 8/1989 | Larsson | 604/74 |
| 4,929,229 A | 5/1990 | Larsson | 604/74 |
| 5,009,638 A | 4/1991 | Riedweg et al. | 604/74 |
| 5,049,126 A | 9/1991 | Larsson | 604/74 |
| 5,100,406 A | 3/1992 | Panchula | 606/74 |
| 5,941,847 A | 8/1999 | Huber et al. | 604/74 |
| 6,273,868 B1 | 8/2001 | Nordvik | 605/74 |

FOREIGN PATENT DOCUMENTS

| | | |
|---|---|---|
| DE | 24 51 953 | 5/1976 |
| DE | 28 07 646 | 2/1978 |
| DE | 41 02 634 A1 | 8/1992 |
| EP | 727 234 A1 | 8/1996 |
| FR | 2 380 784 | 9/1978 |
| GB | 533493 | 2/1941 |
| GB | 660283 | 11/1951 |
| GB | WO00/10625 * | 3/2000 |
| SE | CH 659 949 A5 | 5/1983 |
| SU | 1745262 A1 | 7/1992 |
| WO | WO 98/22160 | 5/1998 |
| WO | WO 00/10625 | 3/2000 |

OTHER PUBLICATIONS

"Compression stimuli increase the efficacy of breast pump function", N.P. Alekseev et al., Jul. 7, 1997.

The 4th Bioengineering Symposium, Aiming for emotionally rich society, thesis lecture, published Jul. 17, 1995.

"Dynamics of Human Milk Extraction: A Comparative Study of Breast Feeding and Breast Pumping", C. Zoppou et al., © 1997 Society for Mathematical Biology.

"Comparing Breastfeeding and Breast Pumps Using a Computer Model", Christopher Zoppou et al., published Mar. 25, 1997.

* cited by examiner

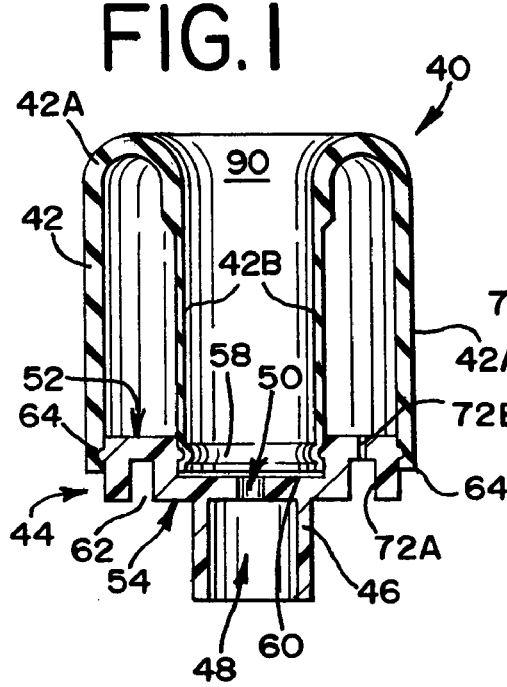
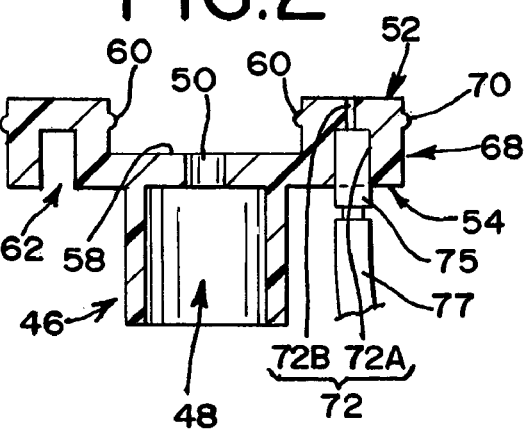
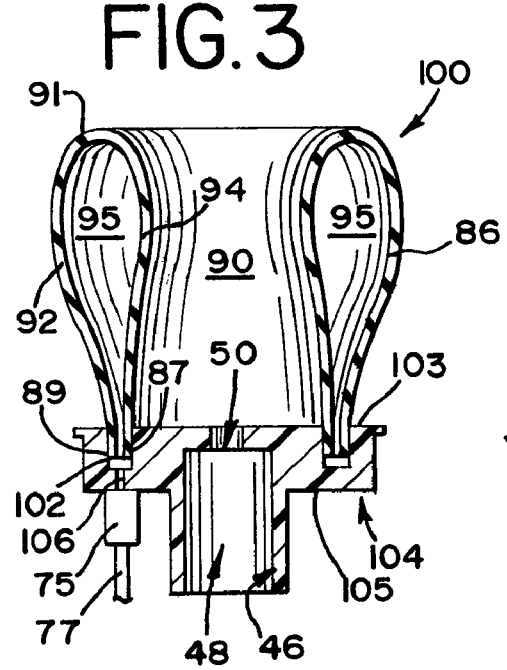
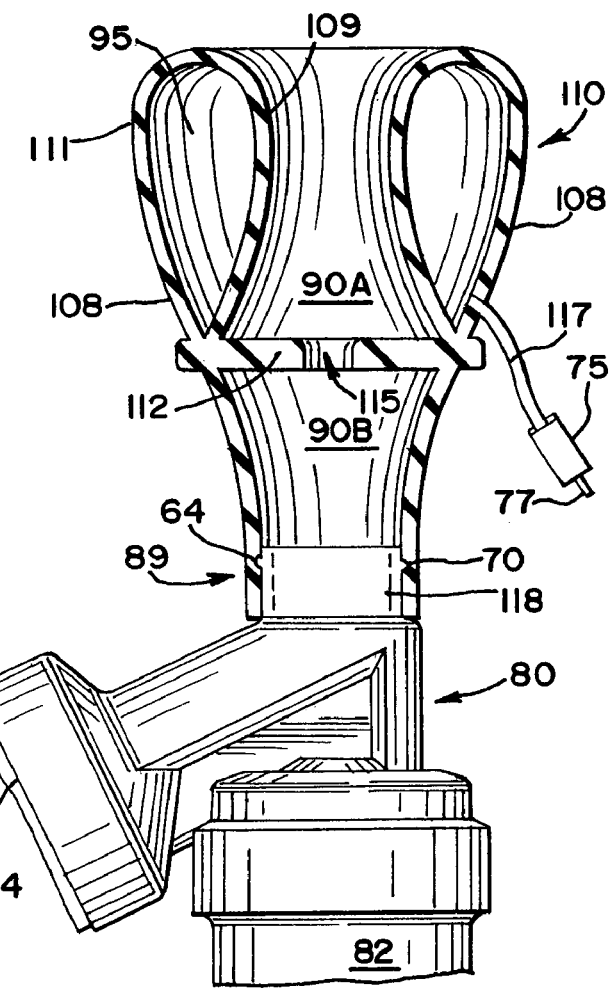

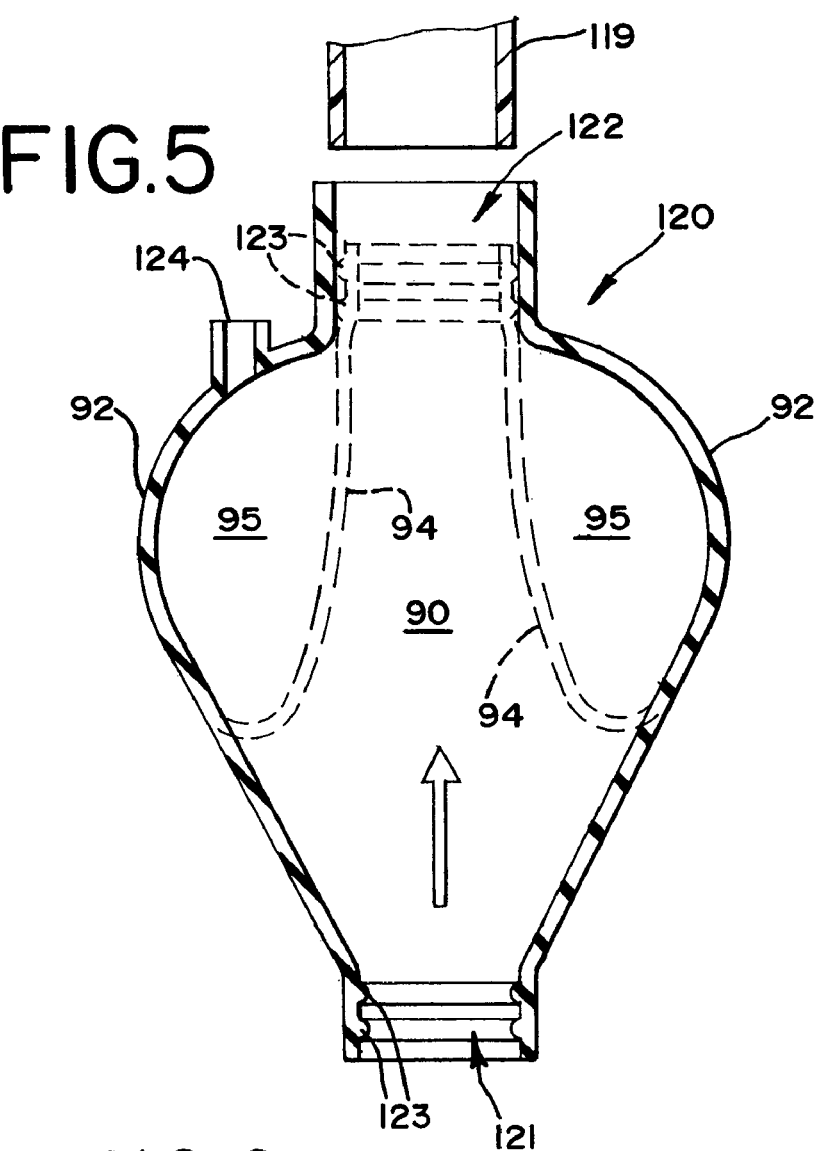
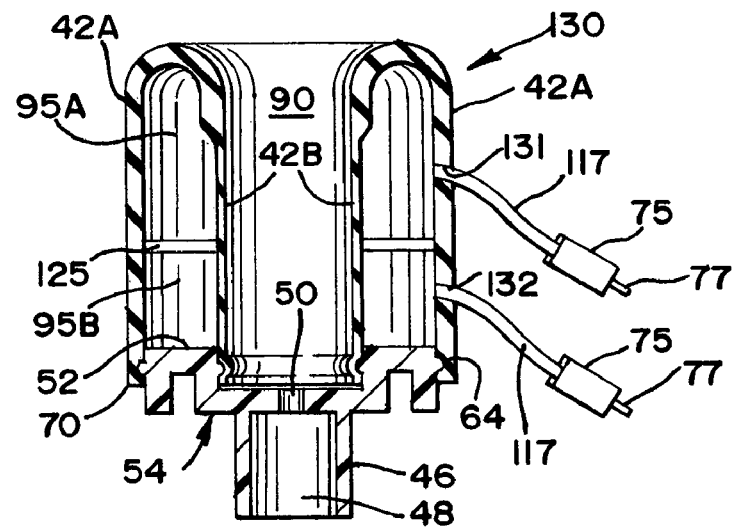

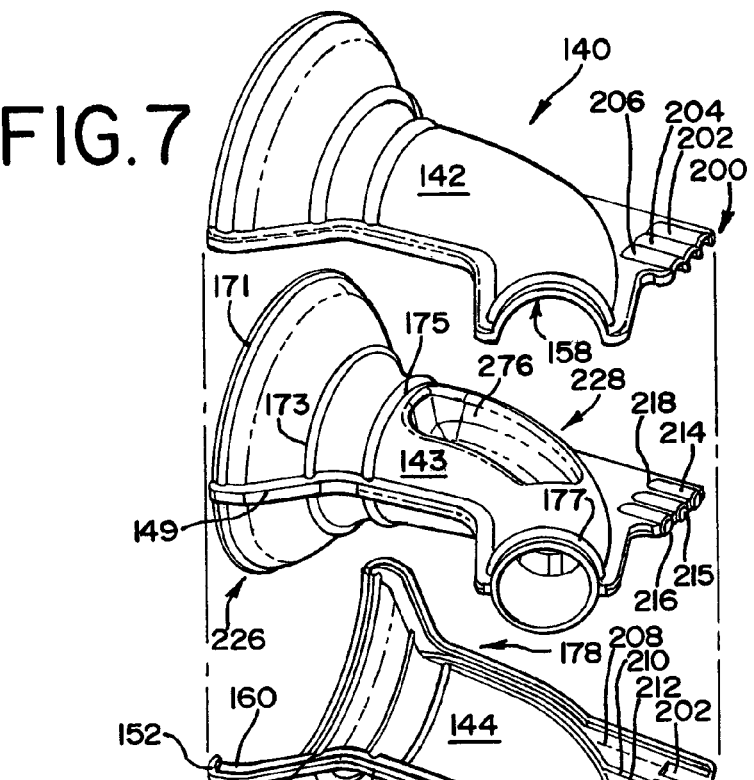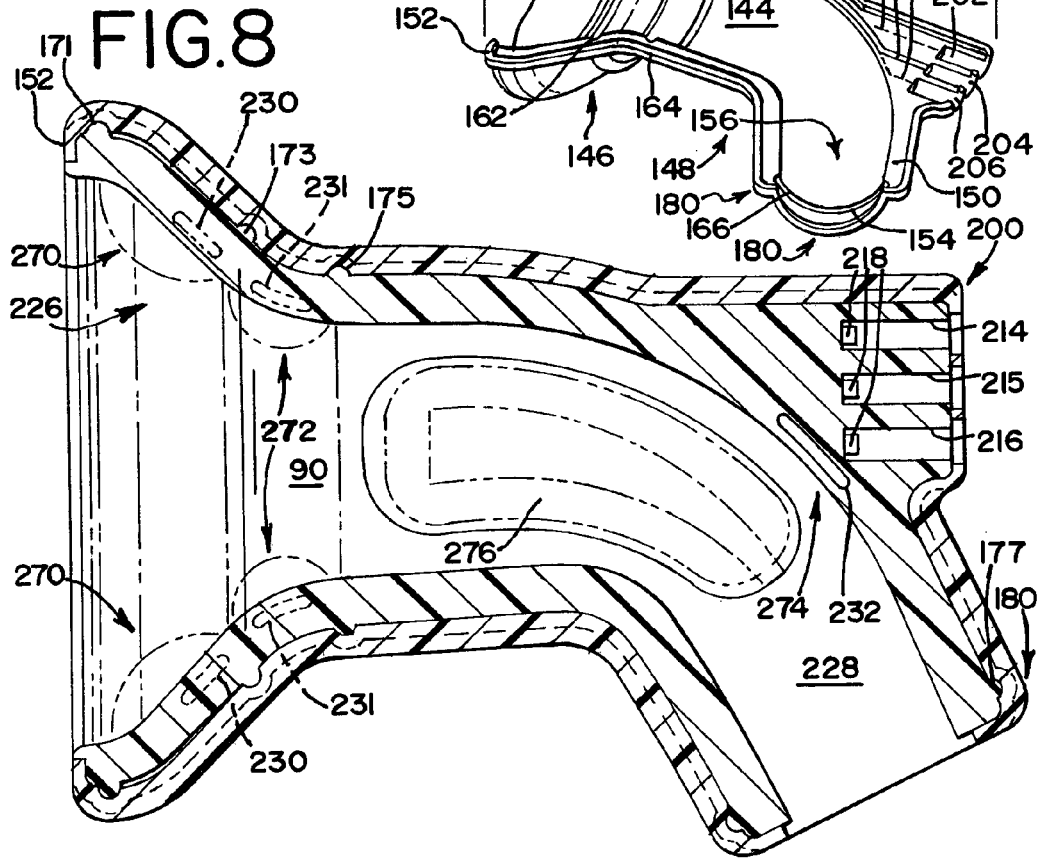

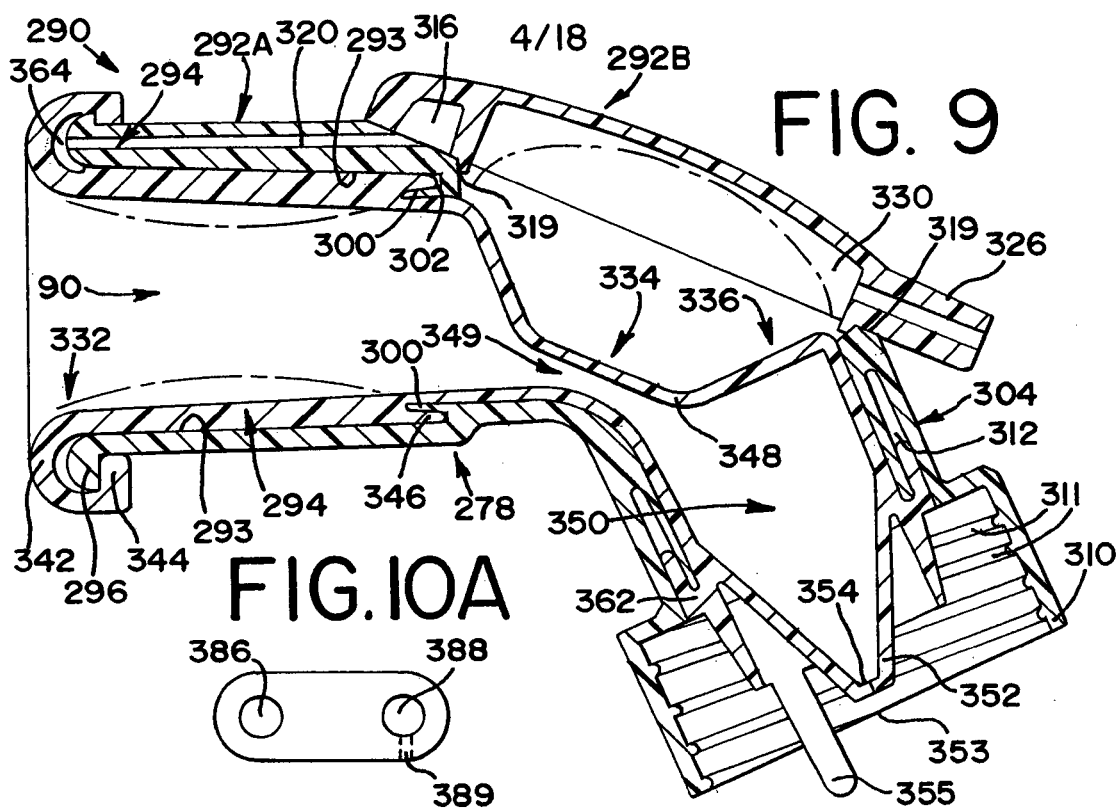
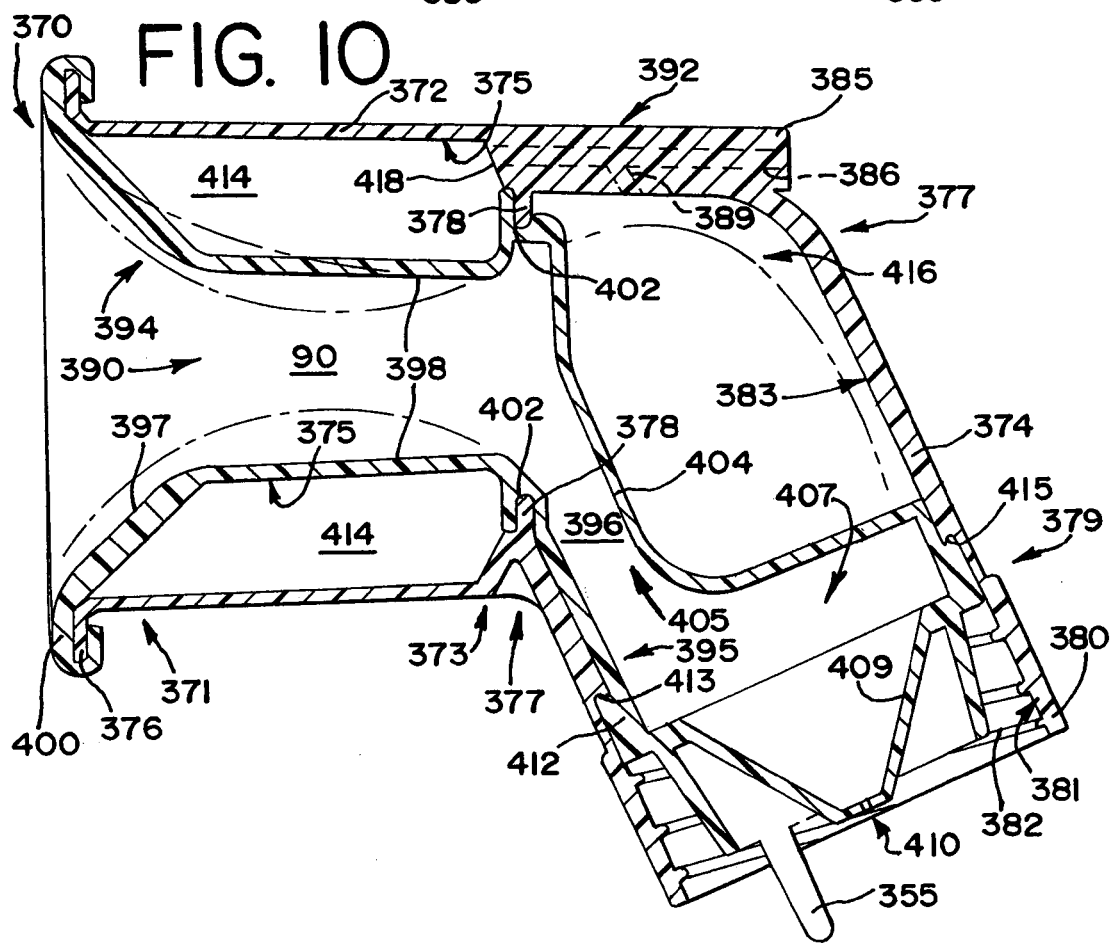

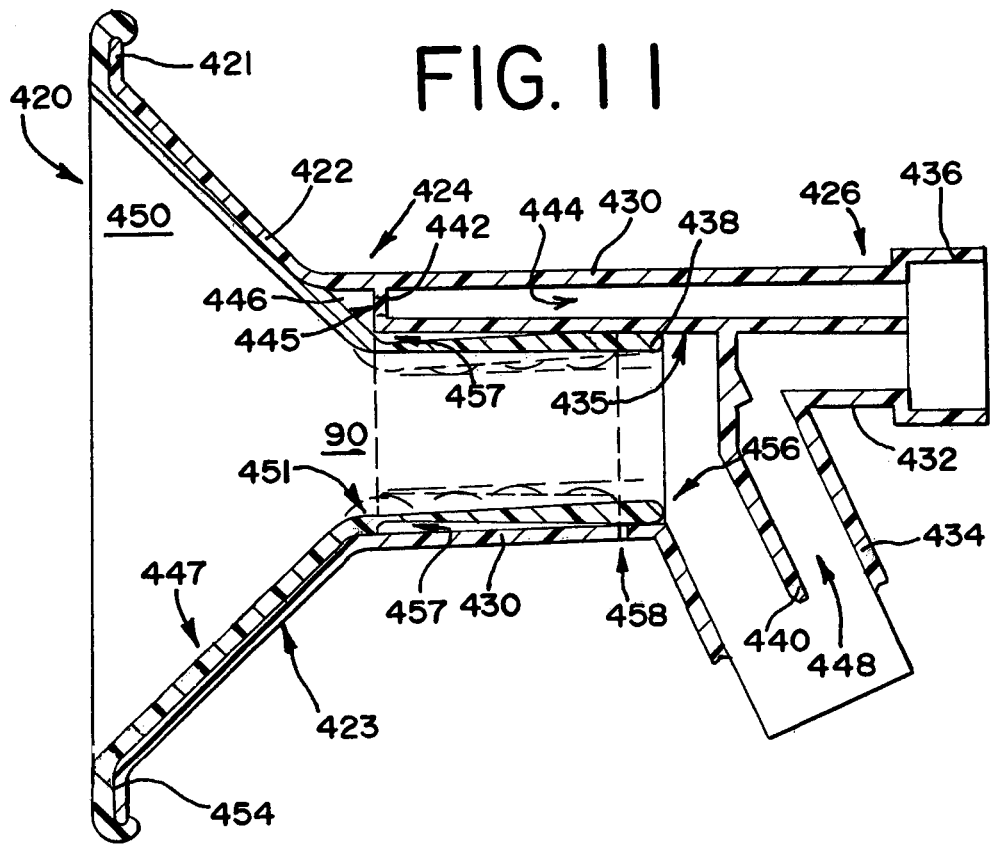
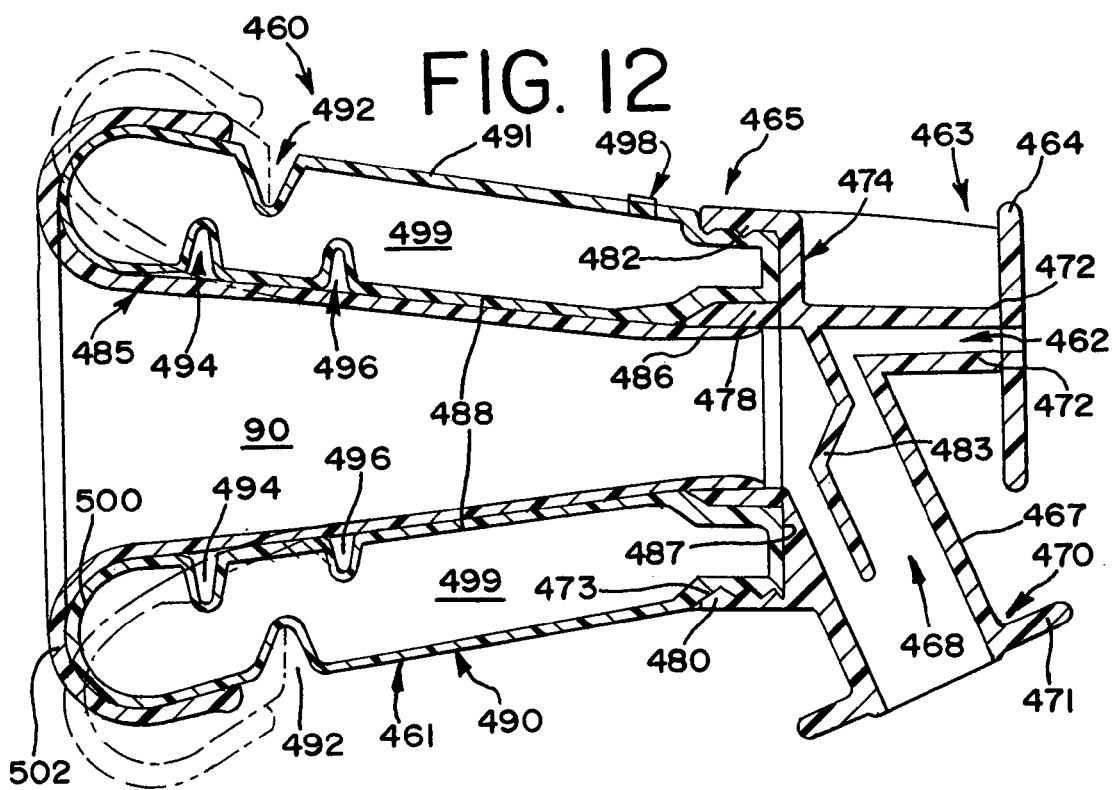

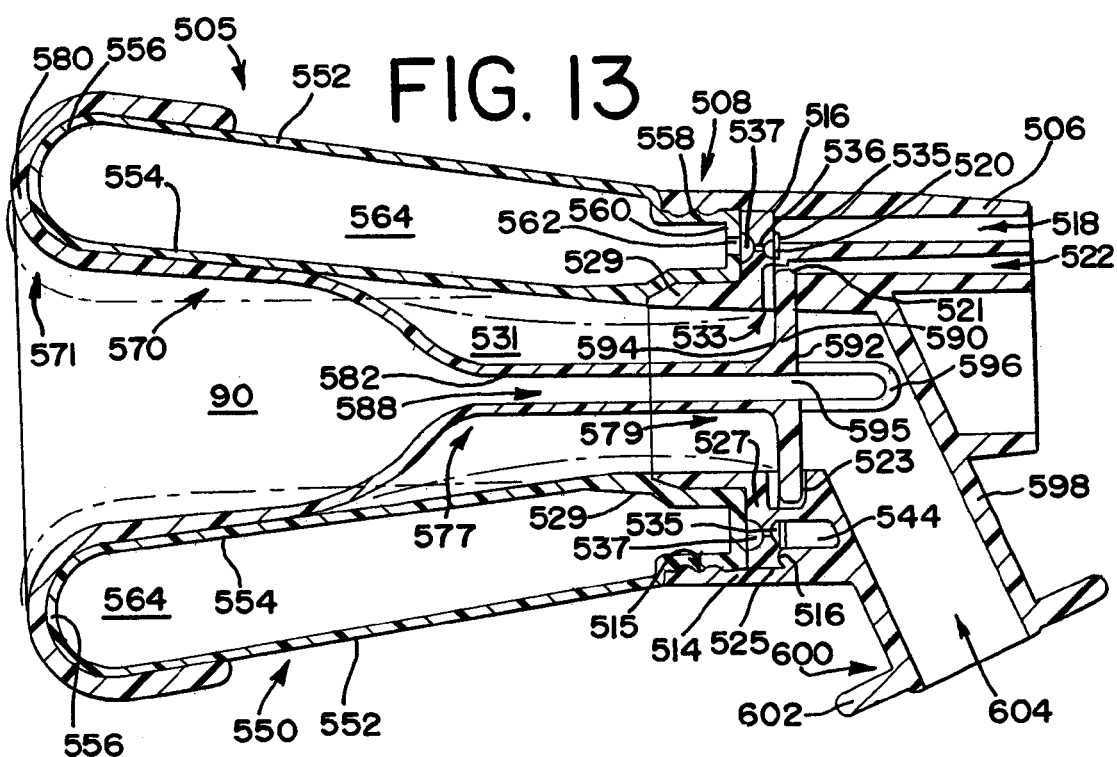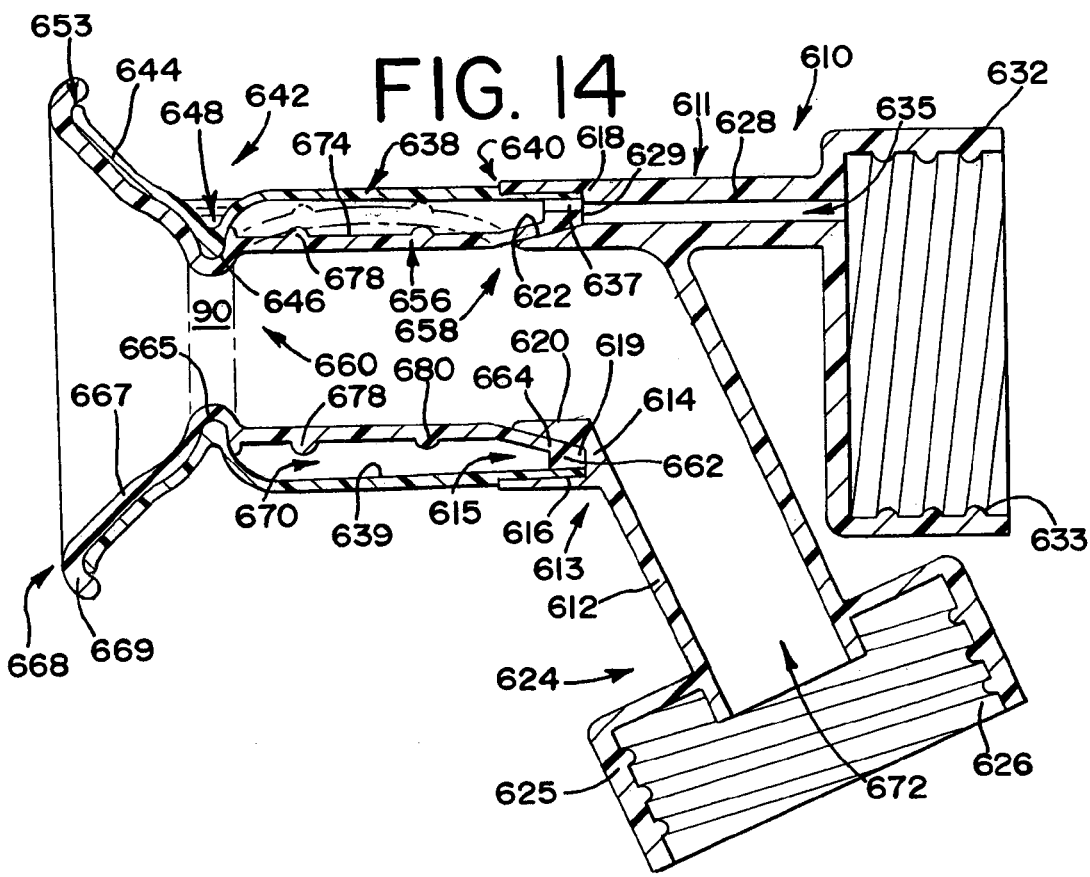

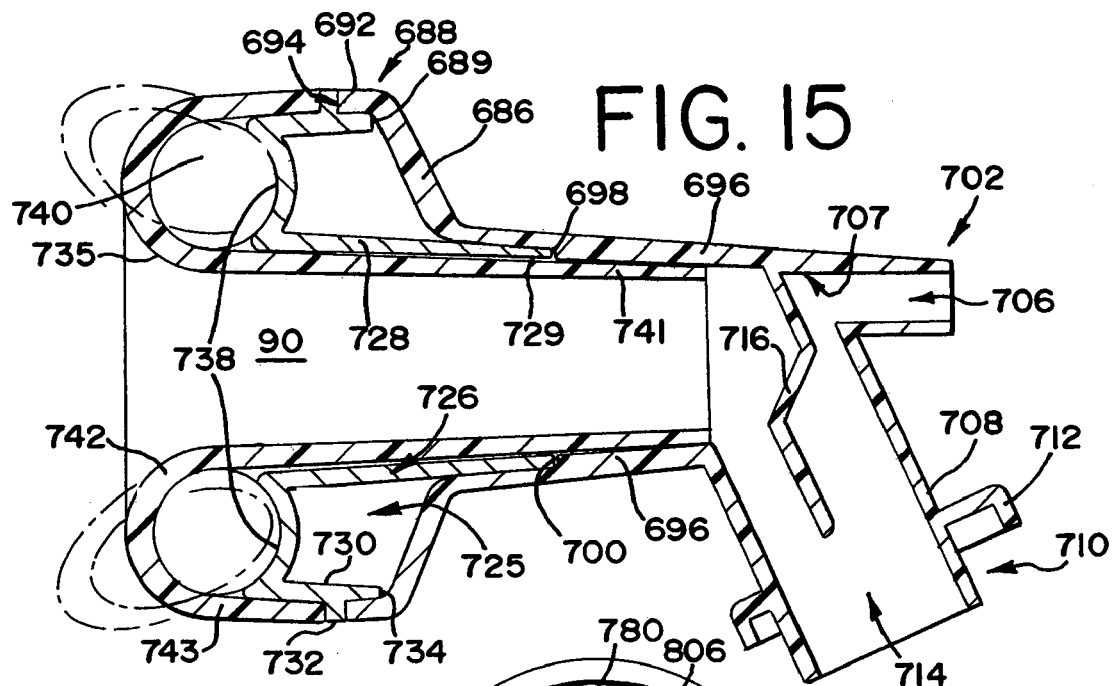
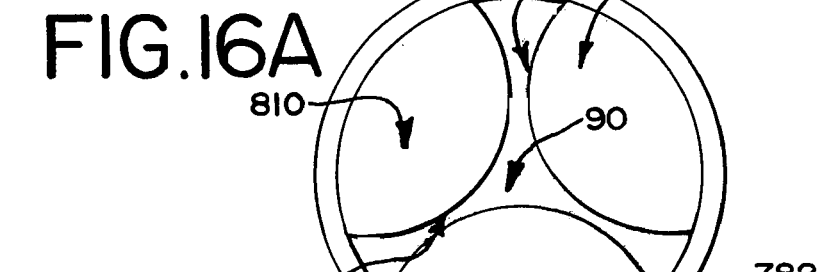
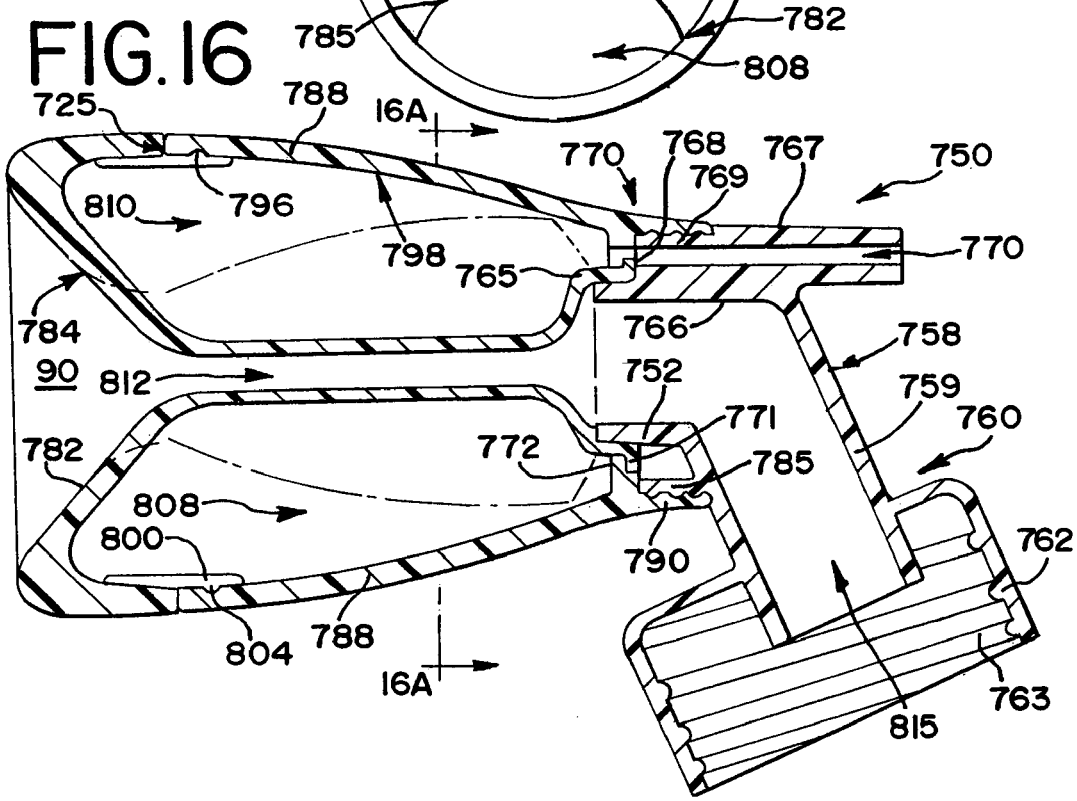

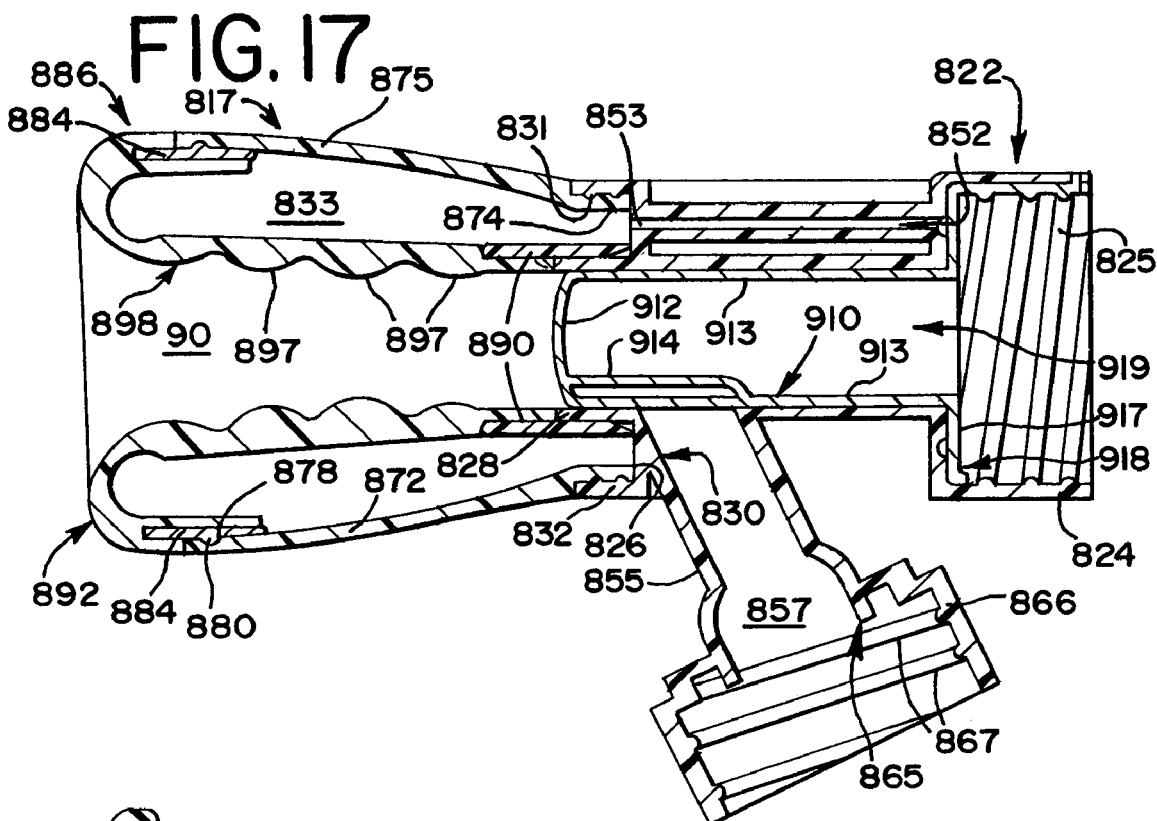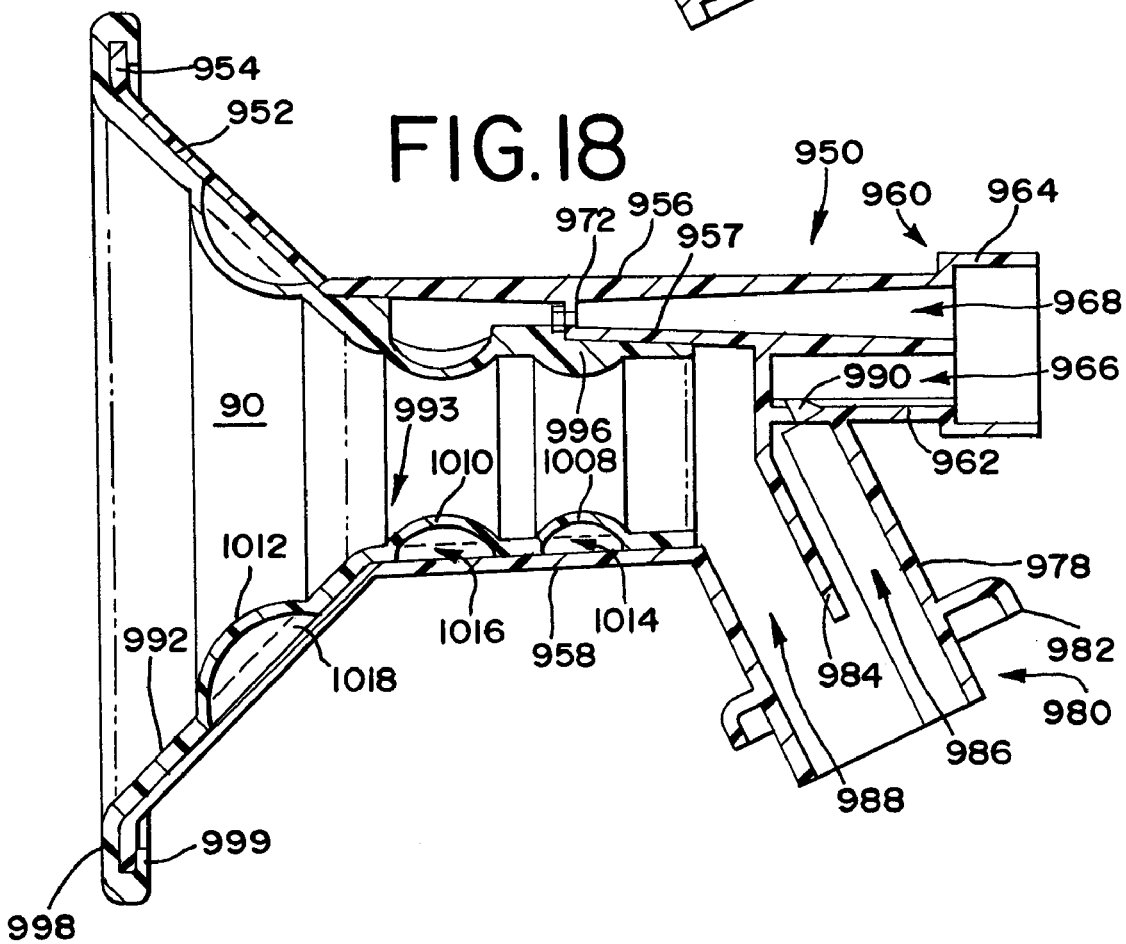

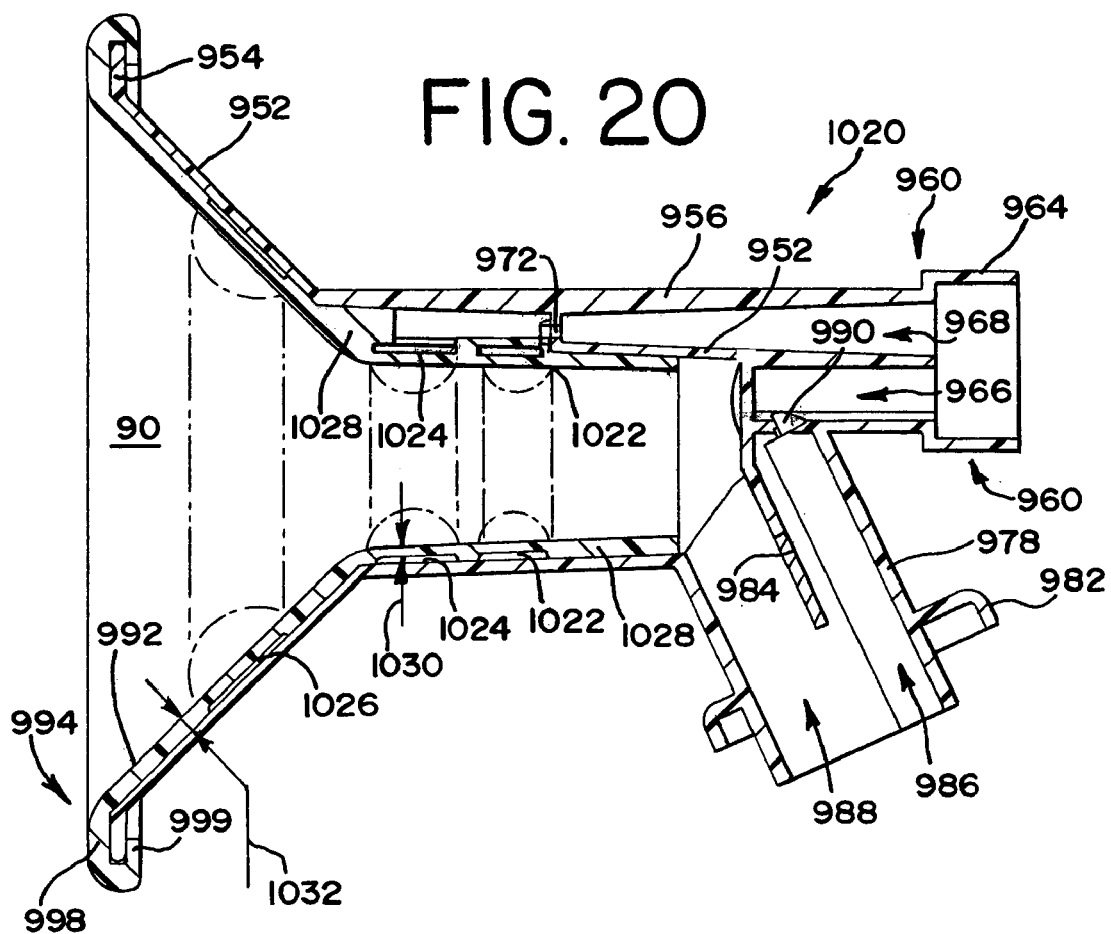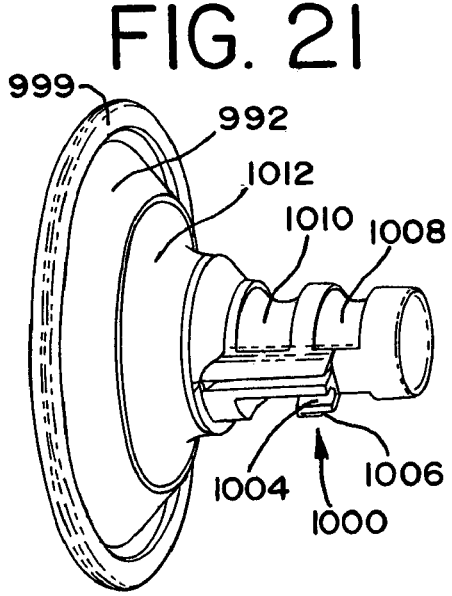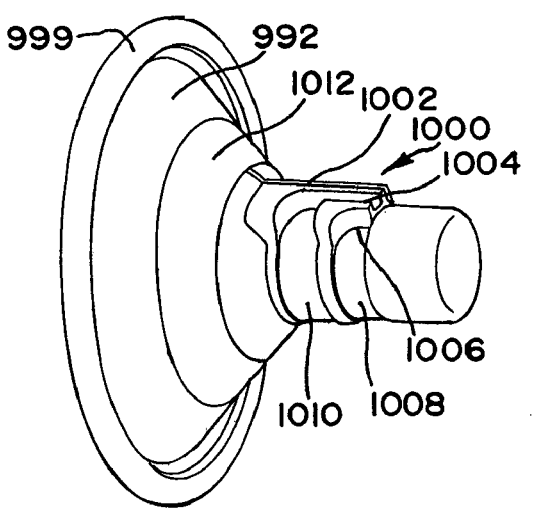

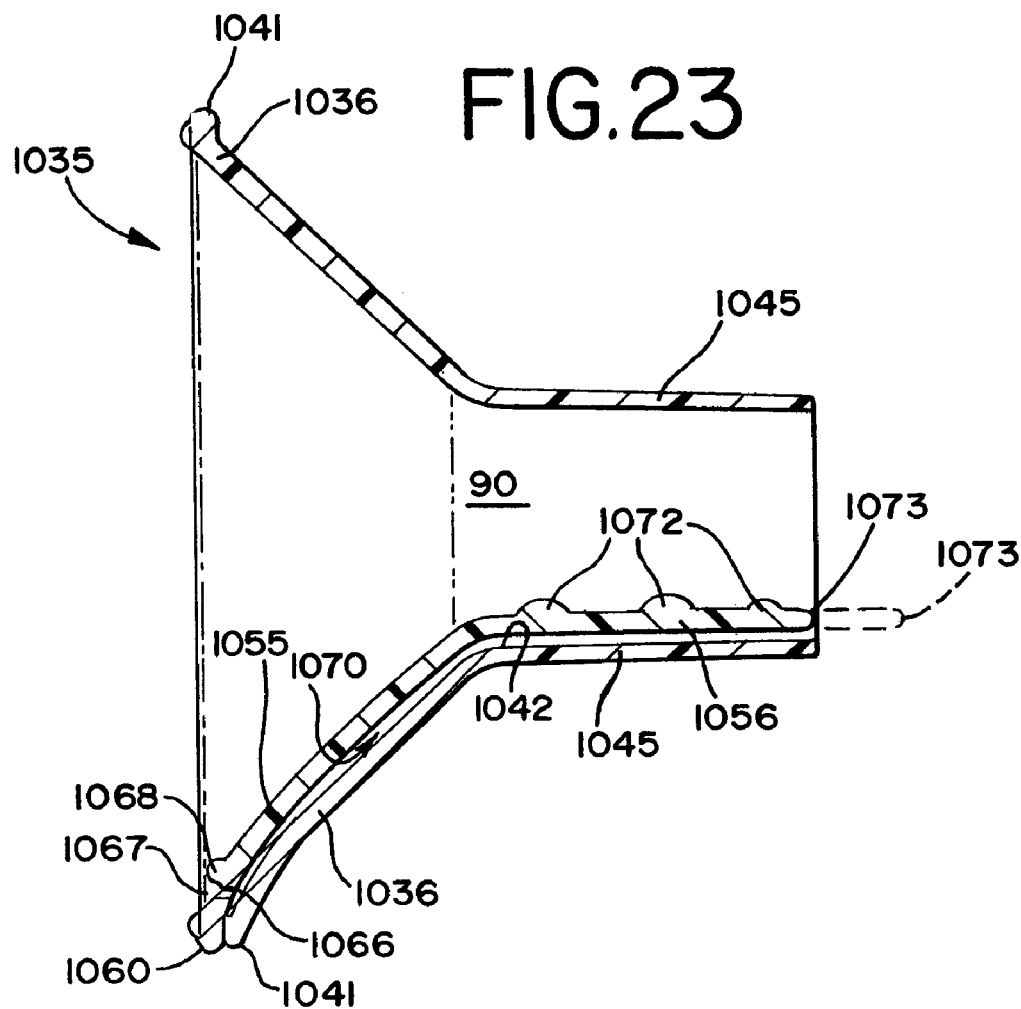
FIG.23
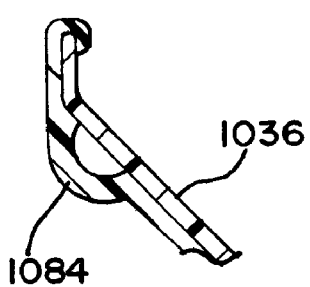
FIG.24A
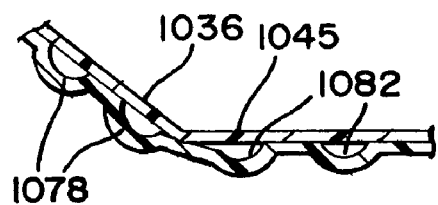
FIG.24B
FIG.24C

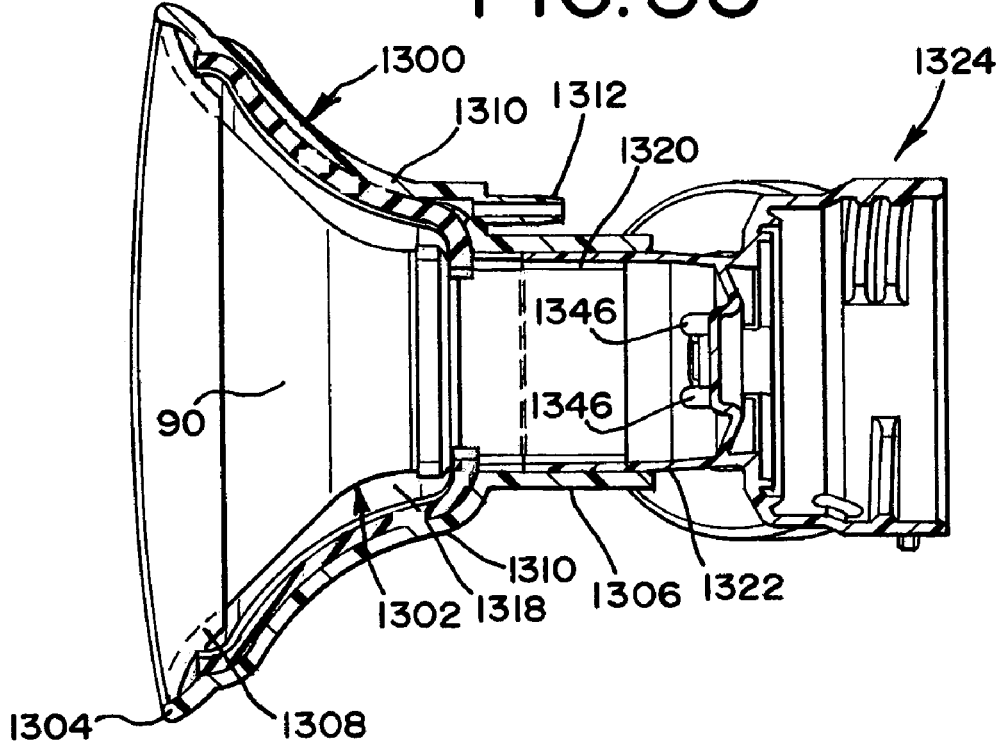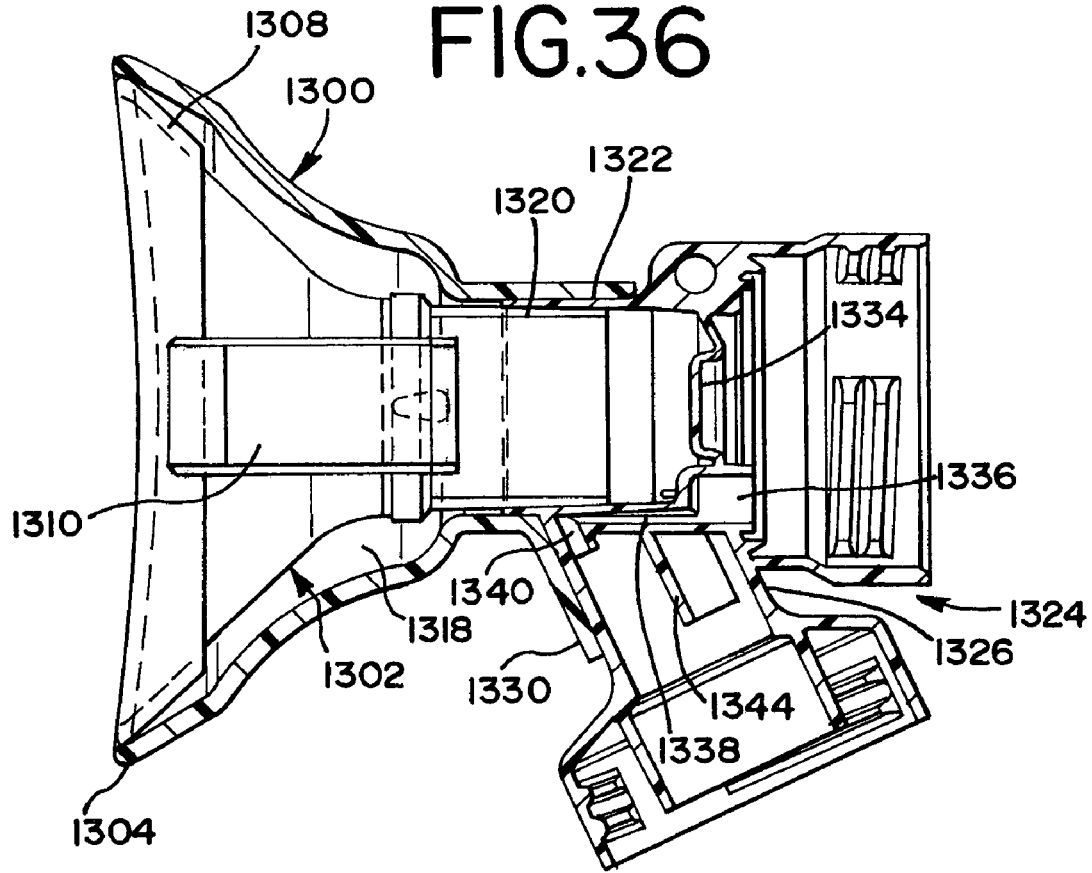

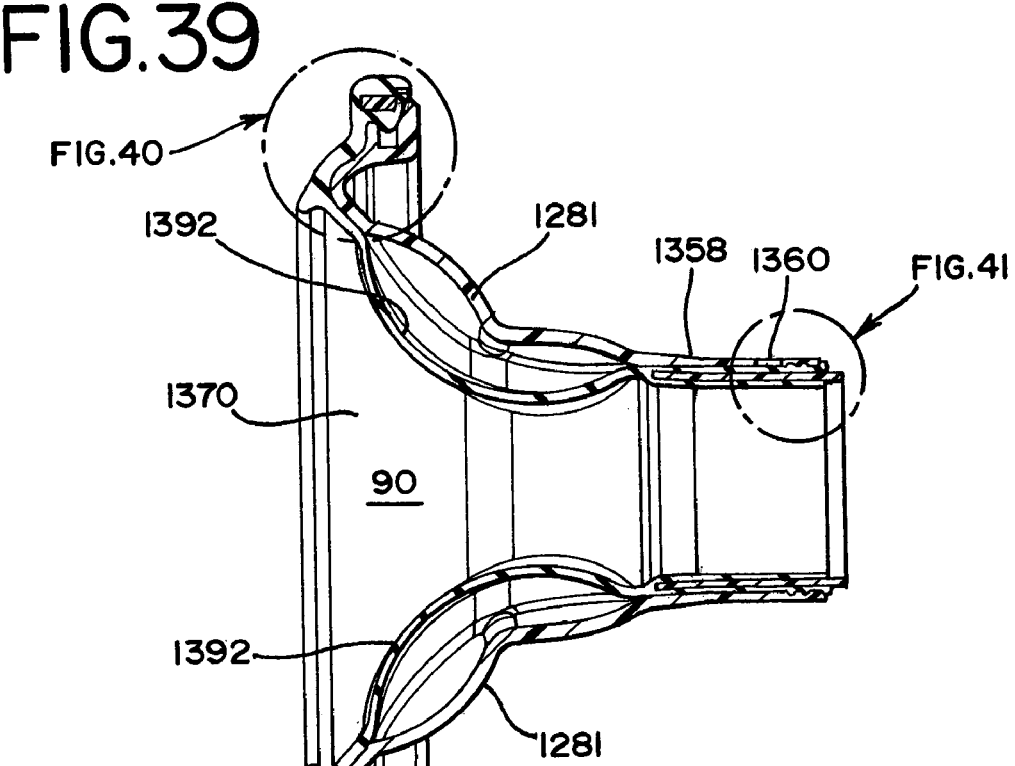
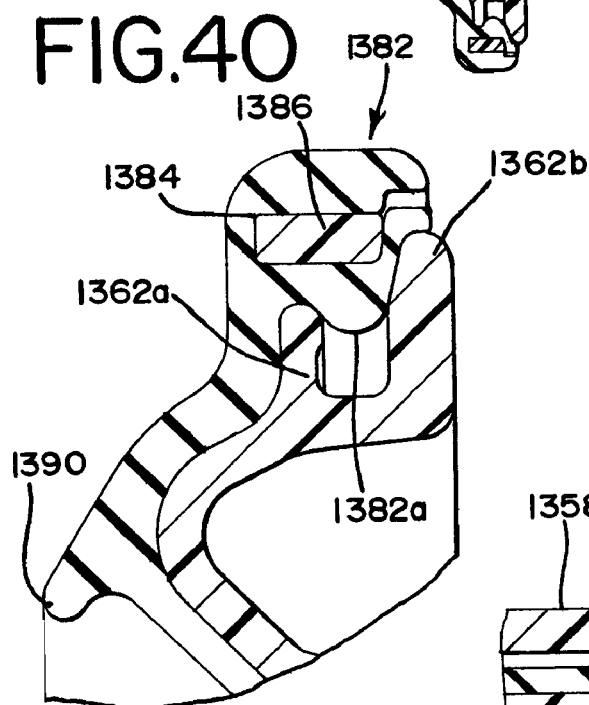
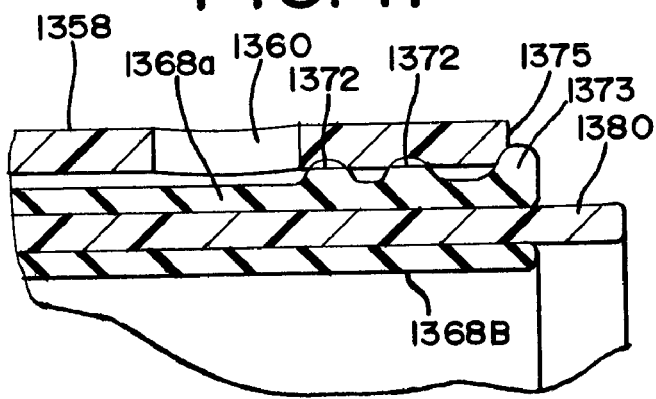

BREASTSHIELD WITH MULTI-PRESSURE AND EXPANSIBLE CHAMBER CONSTRUCTION, RELATED BREASTPUMP AND METHOD

This application is a Divisional Application of U.S. Ser. No. 09/888,322 filed on Jun. 22, 2001 now U.S. Pat. No. 6,663,587.

FIELD OF THE INVENTION

The present invention relates generally to breastmilk pumps, and more particularly in one aspect to a breastshield apparatus having a capacity for delivering pressure, positive as well as negative, which can be independently applied in varying degrees and/or zones to better simulate the natural suckling action of a baby, among other advantages.

BACKGROUND OF THE INVENTION

Breastpumps are well known, and generally comprise a hood or shield that fits over the breast, and a vacuum pump connected to the shield for generating an intermittent vacuum (negative pressure) within the shield. In its simplest and most common form, an intermittent suction action of the vacuum pump serves to pull on the breast and massage it so as to extract milk. The extracted milk typically drains from the shield into a collection container, such as a baby bottle, which is ordinarily attached directly to the breastshield apparatus.

Inserts for use within the hood or shield of a rigid breastshield assembly are also known, and have been used for sizing the breastshield. That is, an insert would be used in a larger funnel-shaped breastshield to reduce the internal diameter of the cone portion and/or nipple tunnel, for a smaller breast. Some rigid-type breastshields have also sometimes been employed with a flexible breast-engaging portion or device mounted interior of a rigid external support or frame, not so much as a sizing mechanism but in an attempt at improved milk expression as well as comfort. In the latter application, an intermittent suction (negative pressure) is applied in the space between the flexible membrane and outboard support, causing the membrane to cyclically collapse and then return to its rest state, thereby gently massaging the breast and/or the nipple, for milk expression.

In most instances, the pressure applied at the breast is a negative pressure (suction), as noted above. That negative pressure is typically applied to the interior of the breastshield in a singular fashion, that is, without any kind of differential pressure application over the breastshield as a whole. This has ordinarily been done through a cyclic pattern (e.g., intermittent) of suction only. There have also been some efforts to provide a breastshield which has a positive pressure applied at the breast, that is, a compressive force around a portion that is capable of expanding (inflating).

The present invention has its genesis in an improved breastshield, breastpump assembly and method for operating the same, which seeks to combine various attributes of positive and/or negative pressure applications, as well as differential sequencing of how one or both are applied in operation.

SUMMARY OF THE INVENTION

A breastshield for a breastpump has an inner shield part with an interior adapted to receive at least some of a woman's breast including the nipple therein, and an outer shield part outboard to the inner shield part. The inner and outer shield parts are joined to form an enclosure defining a pressurizable chamber. The inner shield part further has at least a portion thereof movable relative to the outer shield part when the chamber is subject to one of a negative and a positive pressure.

A first pressure port is in communication with the chamber for connection with a fluid pressure source of a first pressure. A second pressure port is in communication with the interior for connection with a pressure source of a second pressure. The breastshield is thus capable of being subjected to two different pressures, such as a positive pressure to move (expand) the chamber into the interior, so as to compress or massage the nipple/breast, and a negative pressure in the interior to draw the nipple/breast further therein for the expression of milk. The pressures can furthermore be independently controlled. They could, moreover, alternate being negative and positive through the same pressure port.

It will be understood that the terms negative and positive as used herein are relative terms. A negative pressure could, for instance, merely be less positive than another pressure. Negative pressure in general as applied to the interior space is typically less than ambient (e.g., vacuum), however.

In one aspect of the invention, the flexible inner shield part conforms to and extends substantially along the entire length of a funnel-shaped interior to the outer shield part.

The invention further takes the form of a breastshield for breastmilk pumping having a rigid outer shield part, an inner shield part molded integrally within the said outer shield part, with the inner shield part forming an inner sidewall to the breastshield and thereby defining an interior adapted to receive therein and surround at least some of a woman's breast including a nipple in a substantially airtight engagement with the breast. A flexible area is formed on the inner shield part, which is capable of movement relative to a breast received within the breastshield. This flexible area advantageously extends around a substantial part of the interior.

An expansible chamber is defined between the inner and outer shield parts, with the flexible area in communication with the chamber. A first port communicates with the chamber to connect a source of fluid pressure to the chamber, whereby application of a source of fluid pressure to the chamber causes the chamber to expand under positive pressure and contract under negative pressure to thereby move the flexible area. A second port communicates with the interior, whereby application of a source of negative pressure is communicated to the interior.

One embodiment along the immediately preceding lines has first and second expansible chambers defined between the inner and outer shield parts, with a flexible area in communication with each chamber. The first port communicates with the first chamber to connect the source of fluid pressure to the first chamber, and a third port is in communication with the second chamber to connect the source of fluid pressure to the second chamber. This enables the first chamber to be subjected to one fluid pressure while the second chamber is subjected to another and different fluid pressure.

Another aspect of the invention is an improved breastshield for a breastpump having an inflated bladder forming a generally toroidal part of the flexible inner shield part within which toroidal part a woman's breast is received to extend toward the downstream part. This bladder is moved relative to the breast/nipple.

In yet another aspect of the invention, a breastshield for a breastpump has a base member with a port through which air and milk can pass. A breast receptacle is mounted on the base, and has an expansible chamber device with an inner flexible sidewall which further forms an interior space adapted to receive at least a portion of a woman's breast including the nipple therein. A first port formed in one of the base and breast receptacle is in communication with an interior of the chamber for connection with a source of fluid pressure. A second port formed in one of the base and breast receptacle is in communication with the expansible chamber device for communication with the source of fluid pressure.

The foregoing breast receptacle is formed in a single piece with an inner shield part, an outer shield part spaced from the inner shield part and a smoothly curved top transition part, the inner, outer and top parts thereby defining the chamber surrounding the interior space. Further, the single piece of the breast receptacle can be designed to have an outer shield part with a greater wall thickness than the inner flexible sidewall, such that the outer shield part is relatively rigid compared to the inner shield part. In a modified form, the single piece of the breast receptacle is initially formed as a flexible-walled member enclosing an interior region with opposed first and second end openings to the interior space; the breast receptacle is then provided by causing the first end to be inverted into the interior region and then placed within the second end.

In still another aspect of the invention, a breastshield for breastmilk pumping has a rigid outer shield part, an inner shield part mounted within the outer shield part, with the inner shield part forming an inner sidewall to the breastshield and thereby defining an interior. A flexible area is formed on some or preferably a substantial portion of the inner shield part. The flexible area is capable of movement from a rest position relative to a breast received within the breastshield. A first space is defined between the flexible area and the outer shield part; the term space as used in this context simply implies a region that can either be an existing gap, cavity, etc., or being capable or yielding the same. A first port communicates with the space to connect a source of fluid pressure to the space, whereby application of a source of positive fluid pressure to the first space causes the space to expand to thereby move the flexible area inwardly relative to the rest position, and application of a source of negative fluid pressure to the space causes the space to contract to thereby move the flexible area outwardly relative to the rest position. A second port communicates with the interior, whereby application of a source of negative pressure to the interior causes the breast to be pulled further into the interior.

In another form of the immediately foregoing version, the breastshield further has a second space defined between the flexible area and the outer shield part. The second space is located downstream relative to the breast, and is isolated relative to the first space. The second port communicates with the second space to connect a source of fluid pressure to the second space. The first and second spaces are thus capable of expanding and contracting independently of each other. Of course, a third space can be defined between the flexible area and the outer shield part, and so on.

An embodiment along the same lines has concavities spaced around the interior of the outer shield part, into which the flexible area is pulled under vacuum.

Another aspect of the invention has a breastshield for a breastpump with a flexible breast receptacle part formed with a generally toroidal shape having a U-shaped or teardrop shape cross-section. An expansible chamber is defined within opposing walls of the receptacle part, and an interior is defined within the toroidal shape and is adapted to receive a nipple and surrounding breast of a mother. A base part has the receptacle part mounted thereto. A first port communicates with the expansible chamber for connection of a fluid pressure source thereto, and a second port communicates with the interior for connection of a pressure source thereto. One or both of the ports can be formed in the base part.

The breast receptacle of the foregoing embodiment is advantageously formed from a single piece of flexible material which yields an outboard circumferential sidewall extending into a smoothly curved forward wall and then extending into an inboard circumferential sidewall. The sidewalls are spaced from each other to form the expansible chamber. The forward wall defines an opening into the interior formed by the inboard circumferential sidewall, and the sidewalls terminate in a rearward wall end structure which is mounted to the base part. The rearward wall end structure is preferably removably mounted to the base part. This can be through the use of a rearward wall end structure that is an open ring-shaped channel formed by spacing the sidewalls apart, with the base part having a ring-shaped collar which is received in the ring-shaped channel and upon which the receptacle part is thereby sealably mounted. Another way is to have the rearward wall end structure formed by bringing the sidewalls together to form a ring, with the base part having a ring-shaped well within which the ring is received to thereby sealably mount the receptacle part to the base part.

In most if not all of the embodiments herein, a valve can further be provided between the pressure source and the first port, for one instance. The valve has a first position for maintaining a desired pressure level within the expansible chamber and a second position for releasing the pressure level.

In still another aspect of the invention, a breastshield for breastmilk pumping has a rigid outer shield part made of left and right portions which join together. An inner shield part is mounted within the outer shield part, the inner shield part forming an inner sidewall to the breastshield and defining an interior adapted to receive therein and surround at least some of a woman's breast including a nipple in a substantially airtight engagement with the breast.

A flexible area is formed on said inner shield part, and is capable of movement relative to a breast received within the breastshield. A first space is defined between the flexible area and the outer shield part. A first port communicates with the first space to connect a source of fluid pressure thereto, whereby application of a source of positive fluid pressure to the first space causes the space to expand to thereby move the flexible area. A second port communicates with the interior, whereby application of a source of negative pressure to the interior causes the breast to be pulled further into the interior. Additional spaces, with respective ports, can be defined between the flexible area and the outer shield part, each space being isolated relative to one another, such that the spaces are capable of expanding and contracting independently of each other.

One such space can be an elongated section of the flexible area which extends into the interior. The elongated section is capable of being acted upon by a negative pressure applied outboard relative to the elongated section to thereby move away from the interior, and thereby generate a negative pressure within the interior while also serving to isolate the source of negative pressure from milk expressed within the interior.

The foregoing left and right portions may also be advantageously provided to engage in a clamshell arrangement around the inner shield part. They are releasably connected to enable removal of the inner shield part from the outer shield part.

In still another aspect of the invention, a breastshield and breastpump for breastmilk pumping a rigid outer shield part with an internal funnel-shape including a widened upstream end extending into a tubular portion which terminates in a downstream end. The widened upstream end has a circumferential rim.

A base has a mount within which the downstream end of the outer shield part is received. The base further has a conduit structure formed therein including a milk passageway for milk to flow through the base, as well as a first fluid passageway and a second fluid passageway.

A flexible shield part has a shape generally conforming to that of the internal funnel-shape and is received within the outer shield part. The flexible shield part includes a bladder which presents an internal sidewall defining an interior to the breastshield and which is adapted to receive a nipple and at least some surrounding breast therein in a generally sealing engagement with said flexible shield part.

An expansible area exists between the flexible shield part bladder and the outer shield part. A fluid aperture is formed in the outer shield part which communicates with the expansible area. The first fluid passageway communicates with the interior, and the second fluid passageway communicates with the fluid aperture when the outer shield part is mounted on the base.

The foregoing flexible shield part furthermore can advantageously have a circumferential upstream portion which snap-fits on the rim of the outer shield part, and a downstream portion which extends around the tubular portion downstream end to thereby form a gasket-like structure for the tubular portion facilitating mounting it with the base.

The breastpump of the foregoing embodiment in one form uses a first output as an intermittent negative pressure to draw the nipple and breast further downstream in the interior. A second output is an intermittent positive pressure to move the bladder inwardly relative to the interior.

The present invention will be further appreciated, and its attributes and advantages further understood, with reference to the detailed description below of a variety of presently contemplated embodiments, taken in conjunction with the accompanying drawings, in which:

BRIEF DESCRIPTION OF THE DRAWINGS

FIG. 1 is a sectional view of a first embodiment of a breastshield constructed in accordance with an aspect of the present invention, shown mounted to a special base member;

FIG. 2 is a detailed view in slightly enlarged section of a part of the base member of the breastshield of FIG. 1, with an airtube attached;

FIG. 3 is a sectional view of a second embodiment of a breastshield constructed in accordance with an aspect of the present invention, again as mounted to a special base;

FIG. 4 is a partial sectional view of a third embodiment of a breastshield constructed in accordance with an aspect of the present invention, shown mounted to part of the rest of a generally conventional breastpump apparatus;

FIG. 5 is a sectional view highlighting a construction phase of a modified form of the breastshield of FIG. 3;

FIG. 6 is a sectional view of a fourth embodiment of a breastshield similar in construction to that of the FIG. 1 embodiment, made in accordance with an aspect of the present invention;

FIG. 7 is an exploded perspective view of a fifth embodiment of a breastshield constructed in accordance with an aspect of the present invention;

FIG. 8 is an enlarged sectional view of an assembled embodiment of the breastshield of the invention presented in FIG. 7;

FIG. 9 is a sectional view of a sixth embodiment of a breastshield constructed in accordance with an aspect of the present invention;

FIG. 10 is a sectional view of a seventh embodiment of a breastshield constructed in accordance with an aspect of the present invention;

FIG. 10A is an end view of ports for connection of pressure sources to the breastshield of FIG. 10;

FIG. 11 is a sectional view of an eighth embodiment of a breastshield constructed in accordance with an aspect of present invention;

FIG. 12 is a sectional view of a ninth embodiment of a breastshield constructed in accordance with an aspect of the present invention;

FIG. 13 is a sectional view of a tenth embodiment of a breastshield constructed in accordance with an aspect of the present invention;

FIG. 14 is a sectional view of an eleventh embodiment of a breastshield constructed in accordance with an aspect of the present invention;

FIG. 15 is a sectional view of a twelfth embodiment of a breastshield constructed in accordance with an aspect of the present invention;

FIG. 16 is a sectional view of a thirteenth embodiment of a breastshield constructed in accordance with an aspect of the present invention;

FIG. 16A is a frontal view (looking into) the breastshield shown in FIG. 16;

FIG. 17 is a sectional view of a fourteenth embodiment of a breastshield constructed in accordance with an aspect of the present invention;

FIG. 18 is a sectional view of a fifteenth embodiment of a breastshield constructed in accordance with an aspect of the present invention;

FIG. 20 is a sectional view of a sixteenth embodiment of a breastshield constructed in accordance with an aspect of the present invention;

FIG. 21 is a perspective view of the inner shield part used within the breastshield presented in FIG. 20;

FIG. 22 is a perspective view of the inner shield shown in FIG. 21 rotated 90 degrees around its axis;

FIG. 23 is a sectional view of a seventeenth embodiment of a breastshield constructed in accordance with an aspect of the present invention, although only half of the flexible interior part is illustrated;

FIG. 24A is a partial sectional view of an inner shield part mounted to the outer shield part of another embodiment made in accordance with the present invention;

FIG. 24B is a sectional view similar to that of FIG. 24A showing yet another type of inner shield part;

FIG. 24C is a sectional view similar to that of FIG. 24A showing yet another type of inner shield part;

FIG. 35 is a top plan view in section of a twentieth embodiment of a breastshield constituted in accordance with the present invention;

FIG. 36 is a side view in section of the FIG. 35 embodiment;

FIG. 39 is a top plan view of the FIG. 38 embodiment;

FIG. 40 is an enlarged sectional view of the forward circumferential edge of the FIG. 38 embodiment; and FIG. 41 is an enlarged sectional view of the reward circumferential end of the FIG. 38 embodiment.

DETAILED DESCRIPTION OF EMBODIMENTS OF THE INVENTION

Figure 19A:
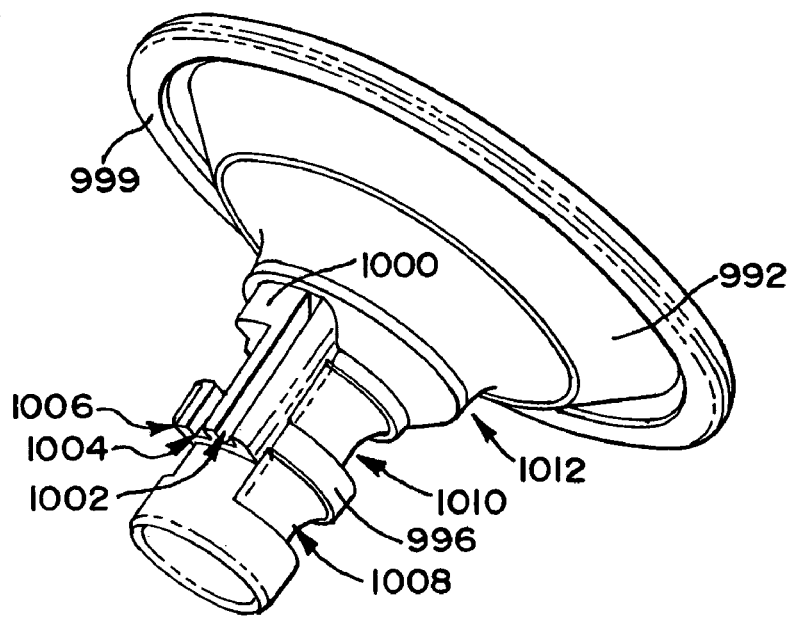
FIG. 19A is a perspective view of an inner shield part used within the breastshield presented in FIG. 18.

FIG. 1 shows a first embodiment of the breastshield of the present invention. The breastshield 40 is formed of a breast receptacle part 42 and a rigid base member 44 which receives the breast receptacle 42. The base member 44 is circular in shape with a centered, downwardly depending tubular extension 46 that includes a larger passageway 48 and a smaller outlet 50, the latter extending into and communicating with the interior of the breast receptacle 42. Base member 44 has upper and lower surfaces 52, 54, which together form a somewhat torus or ring-like shape for the base member 44 between these two surfaces. A well 58 is defined by the inside of the ring, with an interior annular mounting lip or bead 60 projecting into the well, and an exterior annular mounting lip or bead 70 (FIG. 2) extending along the outboard side of the ring. The receptacle part 42 is received and mounted to the base upon these lips 60, 70. The base member 44 further includes an annular undercut 62, which serves to eliminate excess material in manufacture of the base.

In this first embodiment of FIG. 1, the breast receptacle 42 is of a generally flexible material, somewhat rubber-like, and designed to encompass the breast nipple primarily, along with some immediately adjacent breast. The receptacle 42 has a thickened sidewall 42A for the outside and into the inlet to the receptacle, with a thinned sidewall 42B along the interior. The thickened sidewall 42A provides structure for the receptacle to hold its general shape, while the thinned sidewall 42B is more flexible, as will be described in more detail hereafter. A groove 64 is formed along the interior bottom of the receptacle outer sidewall 42A, into which the bead 70 is received; a similar groove may be formed in the interior bottom of the thinned sidewall 42B, or the material itself may have sufficient elasticity to simply fit over the bead 60. It will be seen that the receptacle is thus mounted on the base member 44 in this manner. As will be readily understood, however, the receptacle 42 and base member could be molded as a single piece, or otherwise assembled as an integral whole.

Turning now to FIG. 2 in particular, a negative or first pressure source (suction) would be connected to or otherwise communicate with the tubular extension or passageway 48. This first pressure source could also convey a positive pressure for certain applications.

There is a connection for a second pressure source via a port 72, shown comprised of a larger diameter section 72a in communication with a smaller diameter section 72b. The larger section 72a facilitates connection to a connector 75, as by a simple interference fit, for tubing 77 that communicates with a second pressure source. This second source could be a positive pressure (compression), or a negative pressure, again entirely dependant upon the application and effect desired. It will be noted that the pressure could be any fluid source, such as air or some other gas, as well as a liquid, which could further be hot or cold.

Operationally, the nipple and immediately surrounding breast area will be received within interior space of the breast receptacle 42. Using an exemplary situation where the first pressure source is negative (at 48) and the second pressure source is positive (at 72), negative pressure (suction) is applied via the outlet/passageway 50, 48. This pulls on the nipple and breast. A compressive pressure may additionally be applied from the second pressure source via port 72, causing the thinner, inner sidewall 42B to expand into the receptacle interior 90. Milk is thereby extracted in this manner. Again, and as will be made evident in the various embodiments of the invention described herein, these pressure sources can be selected and applied in numerous ways and combinations. For instance, the second pressure source could initially be positive only after the first suction source has reached a certain level, and then turn negative thereafter. The second pressure source could initially be negative, thus expanding the interior space 90 of the receptacle 42 as the nipple is pulled therein by the suction of the first pressure source, and then the second pressure source goes positive to compress the nipple and breast therein. Many different pressure combinations, cycles and applications are therefore contemplated.

In the FIG. 1 embodiment, the expressed milk initially collects within the well 58, and then passes through the outlet 50 and passageway 48 before being collected in a bottle (not shown in this embodiment, but in FIG. 4, for instance at 84) or other container. Standard and well known valving for the breastpump fluid control (milk and air), and details on other associated breastpump parts and equipment normally used with breastpumping are not disclosed herein, but such are shown in U.S. Pat. No. 4,857,051, for example, which can be additionally referred to for such other details.

FIG. 3 shows a second embodiment 100 of a breastshield that is similar in many respects to that just described. It is seen that the flexible breast receptacle 86 has a generally uniform wall thickness in this version. This breast receptacle 86 could be formed, for example, through a single cut-out piece folded upon itself to yield the interior space 90 defined by interior sidewall 94, and the toroidal-like chamber 95 between the interior sidewall 94 and the exterior sidewall 92. This yields a smoothly curved top transition part 91 to the receptacle between the aforementioned sidewalls. In this second embodiment, ends 87, 89 of the receptacle 86 are secured within an annular slot or channel 102 that is formed in the top surface 103 of a base member 104. However, it should be noted that each end 87, 89 does not touch, at least not all the way around the slot 102, thereby forming a space or gap therebetween, which extends into the chamber 95.

A port 106 is formed in the bottom surface 105 of the base member 104 to communicate the pressure fluid, here positive pressure, through tubing 77 and connector 75. It will be noted that like numbers relate to like parts and elements between the various embodiments.

The inner sidewall 94 is seen to define the interior space 90 that has a diameter which expands radially as one moves along the longitudinal axis toward the outlet 50. A breast/nipple inserted within the interior space 90 will generally result with the nipple being disposed within the widened area of this profile of the interior space. The interior space 90 is in communication with the outlet 50 and the passageway 48 formed in the tubular part 46 of the base member 104. Upon applying an intermittent positive pressure within the chamber 95 and a negative pressure within the interior space 90, the nipple area of the breast which is received in the neck of the interior space, as well as the breast itself, will be massaged by a flexing of the sidewalls of the receptacle toward and away from the breast and nipple, with the nipple being rhythmically pulled upon by the vacuum through outlet 50 into space 90.

FIG. 4 shows another variation, here similar in nature to that of the embodiment presented in FIG. 3. In this third embodiment 110 of the invention, it is seen that the wall thickness is again generally uniform, although it need not be so. However, instead of folding a single piece in the manner of FIG. 3, this breastshield is formed as by molding in its integral shape. The breast receptacle 111 has flexible inner and outer sidewalls 109, 108 respectively, which define a toroidal-like chamber 95 therebetween. The "ends" of the sidewalls 108, 109 are integrally joined with a partition part 112, thereby dissecting the interior space of the receptacle 111 into an upper section 90A and lower section 90B. The partition part contains an outlet 115 centrally located therein.

The upper section 90A is in fluid communication with the outlet 115, which is also in communication with the lower section 90B of the interior space. The lower section 90B is in communication with a negative pressure source (vacuum). Tube 117 extends into the chamber 95 of this third embodiment 110, and is fixed in the sidewall 108. Tube 117 is connected via a tube connector 75 to tubing 77, the latter connectable to another source of pressure, such as a positive pressure source. Again, although a negative pressure source will in all likelihood be in communication with the sections 90A, 90B at some point in the process, this does not exclude the application of positive pressure to the same at another point in the cycle; likewise, a negative pressure could be applied to the chamber 95. The negative pressure can be used in chamber 95 to create a "vacuum" condition within sections 90A and 90B. Connector 75 could also be a valve, such as a one-way valve, with a pressure-release aspect to adjust the pressure in chamber 95.

Within the lower section 90B, a collar 118 is part of the breastpump 80, and it is upon this collar 118 that the third embodiment 110 of the inventive breastshield is mounted. The exterior of the collar 118 has an external bead 70 which is received within a complementary groove 64 formed in the neck 89 of the downstream end of the breastshield 110. Of course, other means to mount or otherwise connect the breastshield to the rest of the breastpump assembly could be used, such as a snap-fit, threaded engagement or the like.

Milk passing through the outlet 115 goes through section 90B into the collar 118, then through internal conduit structure to the bottle 84. In this embodiment, a manual piston pump 82 is illustrated as the source of negative pressure communicating with the receptacle interior 90A; details of such a piston pump, as well as the breastpump assembly in general, can be gleaned from U.S. Pat. No. 4,857,051.

As with the previous embodiments, the chamber 95 is inflated and deflated in a desired manner, with the application of a periodic suction force in the receptacle interior 90A/90B. A woman's breast received within the interior space of the receptacle of the breastshield 110 would be massaged by the flexing action of the inner sidewall 109, expressing milk from the breast.

Referring to FIG. 5, yet another embodiment of a breastshield is shown which is reminiscent of the FIG. 3 embodiment, and to an extent the methodology that will be described for forming the breastshield is also applicable to the embodiment shown in FIG. 1. As illustrated in FIG. 5, the breastshield 120 is formed of a flexible walled member having a first open end 121 and second open end or neck 122. A pair of spaced apart beads 123 are provided around the interior of the first open end 121. It is intended that the breastshield would be initially formed as by molding in the shape shown in solid line in FIG. 5. It should be noted that the exterior sidewall 92 could be made semi-rigid to rigid, at least in part (i.e., the part that will remain on the outboard side).

Construction of the breastshield of FIG. 5 then involves the inversion of first open end 121 into an interior region of the flexible wall member with it then being pulled toward and into the second open end 122, along the direction of the heavy arrow depicted in the figure (the longitudinal axis). The beads 123 engage and grip the inside of the sidewalls defining the neck 122 through the inversion process. It may be noted that grooves for receiving the beads 123 could also be provided around the inside of the neck 122. A breast receptacle formed as a result of the foregoing process presents a single, integral member having an inner sidewall 94 that now defines an interior space 90 for receiving the breast and nipple. Interior sidewall 94 and exterior sidewall 92 combine to form toroidal-like chamber 95. A port 124 is provided for attachment of a connector/tubing for application of a pressure source to the chamber 95. The breastshield formed by the FIG. 5 embodiment would be attached to a collar 119 similar to collar 118 previously described.

FIG. 6 shows another embodiment 130 which is similar to that of FIG. 1. In this fourth embodiment 130 of the invention, an internal ringlike divider 125 is provided to define upper 95A and a lower 95B sections or chambers inside of the breast receptacle. The upper chamber 95A and lower chamber 95B are isolated from each other, and they include respective ports 131 and 132. Tubing 117 is shown fixed within and extending from each of the ports 131, 132, to which connectors/valves 75 and feed tubing 77 are connectable for communicating positive and/or negative pressurized fluid to the respective chambers 95A, 95B. The pressures within each chamber 95A, 95B may differ, such that one chamber may have a negative pressure therein, while the other chamber may have a positive pressure therein. Both chambers could have positive pressures, though of differing amount, for another example. Again, the pressure and the cycle thereof for each chamber 95A, 95B, as well as that applied to the interior 90 of the breast receptacle, can be selected and adjusted as desired. Like the operation of the previous FIG. 1 embodiment, the inner sidewall 42B is more flexible since it is thinner in cross section than the wall thickness of the outer wall 42A, causing it to flex toward or away from the interior space 90 when the fluid source(s) is applied to one or both chambers 95A, 95B. The flexing of the inner wall 42B causes massaging of the breast and nipple. However, the effect of the two differing pressures and their application in the chambers 95A, 95B, along with a suction force applied to the interior 90, can be uniquely tuned, such as in ways that would be more closely simulating a baby's actions while feeding.

Turning attention now to FIGS. 7 and 8, another embodiment of the present invention will be described. As best seen in FIG. 7, the breastshield 140 of this fifth embodiment is comprised of a rigid outer shield part having a first half 142 and a second half 144, with an elastomeric and flexible inner shield part 143 interposed therebetween. The first and second outer shield halves 142, 144 are complementary mirror images to each other, therefore, only the lower or second half 144 of the rigid shield that is shown in FIG. 7 will be described in somewhat greater detail.

As seen, the rigid outer shield 142, 144 is comprised of a funnel section 146 and an integral curved tubular section 148. Surrounding the perimeter of the outer shield is a peripheral flange 150, which facilitates snap-fitting each half 142, 144 together, while also capturing a complementary flange 149 of the flexible inner shield 143. Alternatively, each half can be molded such that a single or common flange side is integrally connected together in a manner that would also be well known, thereby providing a clamshell effect for joining the two halves. The forward end of the rigid outer shield is formed with a smooth, inwardly curved lip 152 that abuts against the breast of a user when a breast is received within the breastshield 140. Alternatively, the front end of the soft part can be extended forward to provide a more comfortable contact with the breast. The other (rearward) end of the outer shield is formed with an annular collar 154 which may be provided with internal threads, a snap-fit means or some other means for connecting the collar, and thus the breastshield 140, to the remainder of the breastpump assembly, including a milk collection container (not shown).

Each half 142, 144 is also provided with a series of corresponding, longitudinally spaced, radial grooves 160, 162, 164, 166 that are formed in the respective interior walls 156, 158 of the halves. The radial grooves form curved seats when the two halves 142, 144 are secured together (see FIG. 8). The seats preferably have a hemispherical cross sectional configuration to receive respective beads 171, 173, 175 and 177 formed on the outboard side of the inner shield part 143.

The first groove 160 is located adjacent the lip 152 that is formed on the funnel section 146. The second groove 162 is also disposed on the funnel section 146 at the opposite, diametrically smaller end, adjacent to the area where the funnel section 146 and curved tubular section 148 transition. The third groove 164 is disposed near the top end 178 of the curved tubular section 148. The fourth and final channel 166 is located at the bottom end 180 of the curved tubular section 148. When the halves 142 and 144 are joined, each of the seats will receive therein a respective bead 171, 173, 175, 177 that is integrally formed on the inner shield part 143, which serves to anchor and position the inner shield part 143 within the rigid outer halves.

The outer shield also includes an integral ported section 200 projecting from the tubular section 148. The ported section 200 is provided with a first, second, and third pressure ports 202, 204, 206, each of which is connected with a respective first, second, and third channel 208, 210, 212 (channels 208 and 212 being shown only partially in dotted line, for better clarity of description herein). Each channel will form a conduit for fluid pressure dedicated to a particular pressure zone in the breastshield, as will be described shortly below. In the concept of this embodiment, each channel would be formed in one (or both) halves 142, 144, and would be open along the inboard side thereof. The elastomeric inner shield part 143 is sized to press against the insides of the halves, thereby closing the open inboard side of the foregoing channels, and completing the conduit structures leading to the respective pressure zones.

The three pressure ports are identically formed within each half 142, 144 and are cylindrical in shape. The inner shield part 143 has three complementary ports 214, 215, 216 formed therein, which are received within the ports of the outer halves. At the inboard ends of the inner shield ports 214, 215, 216 are outlets 218. These outlets communicate with the channels in the outer halves. Connectors/tubing for communicating air or other fluid pressure would be attachable at the ports 214, 215, 216. As will be evident, the pressure being applied to a particular zone can be different or the same as another zone. The conduit to each pressure zone terminates at the inner sidewall 156, 158. Of course, the number of zones can be increased or decreased, as desired.

As mentioned above, the breastshield 140 has a flexible elastomeric member which forms the inner shield part 143. The inner shield part 143 has a generally complimentary configuration to the first and second halves 142, 144, comprising a conical section 226 and a tubular extension section 228. The inboard side of the inner shield part 143 defines the interior space 90 which receives the woman's nipple and breast.

A first pressure zone 270 is located on the conical section 226 generally between the first 160 and second 162 annular seats. A second pressure zone 272 is located further downstream from the first pressure zone 270 generally between the second 162 and third 164 annular seats. The third pressure zone 274 is located more on the tubular extension 228. The first pressure zone 270 is defined by an expansible chamber in the form of an inboard bulging area at 230. This could be a thinned inboard part (i.e., facing into the interior 90) thereby produced in the sidewall structure. Upon application of a positive pressure conveyed through the channel/conduit 208 to the area 230, as by an aperture (not shown) into region 230 aligned with the end of the channel/conduit, this sidewall which is now defining the first pressure zone 270 will expand inwardly, i.e., into the interior 90, as shown in dotted line in FIG. 8. Release of the pressure returns the sidewall to its rest or original position.

The second pressure zone 272 is defined and operates in a like manner. Second pressure zone 272 has an area 231 of the inner shield part 143, which is in communication with channel/conduit 210.

The inner shield part 143 in this embodiment also includes a pair of opposed indented portions 276 integrally formed within the tubular extension 228. Each indented portion 276 may do no more than simply serve as a tactile surface against which the nipple and breast will lightly rub under the action of suction applied within the interior 90. However, under negative pressure from a pressure source at channel/conduit 206 in communication with the outboard side of the indented portions 276, the negative pressure operating on the outboard side of the indented portions 276 serves to flex them outboardly. This generates a negative (suction) pressure in chamber 90, while also serving to isolate the vacuum source. Indented portions 276 can thereby be inflated/deflated as desired through pressure conveyed via channel/conduit 212 in this modified form.

In operation of the foregoing embodiment of FIGS. 7 and 8, a woman's breast is inserted into the interior space (chamber) 90 of the breastshield 140, and a generally airtight seal is created thereabout with the interior sidewall of the inner shield part 143, as for instance around perimeter 152. The woman's breast and nipple extend into the interior space 90 such that the nipple is generally received at or between the flexible indented portions 276. A positive pressure fluid source (not shown) is, for one example, connected to the first and second pressure ports 202, 204, and thus to zones 270 and 272, with negative pressure also being supplied to the third pressure port 206 to the third zone 274 (i.e., creating a suction force within interior space 90). The positive pressure fluid (e.g., air) source would be intermittently applied to the pressure zones 270 and 272, as would the suction force applied to the interior 90. Application of the positive pressure causes the elastomeric inner shield part 143 at those zones to expand in toroidal fashion into the interior space 90, as seen in dashed-line form in FIG. 8. The expansion of the flexible area into the interior space 90 causes a compression/depression of, and massaging effect upon, the breast. With a negative pressure intermittantly applied to the interior space 90, the flexible indented portions 276 will cyclically flex under the influence of that negative pressure toward and away from the nipple of the breast, also causing nipple stimulation upon contact, which is considered to further increase the expression of milk from the breast.

The sequencing of the pressure application, along with the rate and amount of pressure being applied, in each zone can be independently established and controlled. This would in all likelihood be preset by the manufacturer, but some variability by the user could also be provided. A single pressure generator (pump) could be used for both the positive and negative pressures utilized, with appropriate pressure regulators and valving being employed for the various pressures being applied to the zones. All of the details regarding the general equipment for vacuum/positive pressure generation, and related tubing for transferring the same to the breastpump assembly and breastshield, is well within the skill of the art.

Turning attention to FIG. 9, a sixth embodiment 290 of the invention is presented. In this embodiment, the breastshield is formed of a rigid, two-piece outer shield part 292A, 292B and a flexible inner shield part 294. The first piece of the rigid outer shield part is a main breastshield housing 292A and the second piece is a lid 292B which attaches to the housing 292A and can be removed for cleaning or assembly of the breastshield 290. Alternatively, the housing may be a one-piece housing where the lid portion is ultrasonically welded or otherwise secured to the main body portion to form an integral unit.

The rigid housing 292A includes a front portion formed as a cylinder which defines a breast receptacle portion of the housing that is associated with an area where a user's breast will be primarily received. The upstream end of the cylinder includes an outwardly curved lip or rim 296, and the lower or downstream end 298 includes an internally disposed, upwardly projecting annular ridge 300 that is spaced from the inside wall surface 293 of the cylinder so as to define an annular groove 302. The annular groove 302 and the lip 296 collectively anchor and position the flexible inner shield part 294 securely within the rigid outer shield part 292A via an annular lip or flange 346 which extends around the flexible inner shield, and which is received within the groove 302, and a groove defined by the front end of the flexible inner shield at 342 and 344 which snap-fits over the lip 296.

A rearward (downstream) part of the housing 292A comprises an extension portion 304 generally comprised of a cylindrical tube, downwardly depending from the lower end 298 of the forward housing 292A. The extension portion 304 has one end integrally formed with a collar 310 thereon for attaching to a milk collection bottle (not shown). The collar 310 may include threads 311 as shown, or it may be provided with a snap-fit mechanism or the like for connection with a bottle.

The lid 292B covers an elliptical area 330 which could just as readily be semispherical or other like shape in housing 292A, which defines a cavity within the breastshield 290. An enclosed channel 316 is also part of the lid 292B, and communicates with a channel 320 formed within, and which extends along the inside of, the breast receptacle portion of the unit. There is an undercut 319 around the perimeter of the lid 292B that allows the lid 292B to snap-fit at this area onto a complementary shoulder of the main housing 292A. The channel 316 communicates with a first pressure port (not shown), whose purpose will shortly be described. A second pressure port 326 is formed in the lid, and this second pressure port directly communicates with the cavity 330. The first and second pressure ports are adapted to connect to a respective pressurized fluid source.

Returning now to the flexible inner shield part 294 of this embodiment, it is formed with a forward part 332, an intermediate neck part 334, and a rearward (downstream) part 336. The forward part 332 comprises the cylindrical segment previously described in regard to its attachment at groove 302 and lip 300 at its rearward end, and is complementary to the shape of the cylindrical wall of the rigid shell in its vicinity. The forward end of the forward part 332 of the flexible inner shield 294 includes a smoothly curved transition part 342 that terminates with an inwardly turned ledge 344, forming a groove or rim. This is received upon a lip 296 of the housing piece 292A, and thereby attaches the inner shield part 294 at this forward part of the housing.

The intermediate neck 334 of the flexible inner shield is integrally formed with the forward and rearward parts 332, 336, so that the entire inner shield is a single piece. The intermediate neck 334 includes a portion which defines a flexible diaphragm 348. As shown in FIG. 9, the rest position of the diaphragm 348 creates a channel 349 through the central region of the inner shield part 294. The channel 349 is in communication with the interior space 90 of the forward part 332 of the inner shield 294, and is as well in communication with a catch chamber area 350 that is defined in the rearward part 336. The rearward part 336 of the inner shield part 294 is formed in a cylindrical shape that is complementary to the cylindrical shape of the surrounding rigid extension 304 from the housing 292A. At the bottom of the catch chamber 350 is a valve mechanism in the form of a duckbill (or flap) valve 352. The valve 352 has a port or slit 353 in its apex 354 for allowing expressed milk from the breast to be conducted out of the catch chamber 350.

The rearward end of the inner shield part is mounted within the rigid housing 292A through the use of another lip or flange 362 formed on the outside of the flexible inner shield which is received within a groove 312 defined in the inside sidewall toward the rearward end of the rigid housing. The rearward end of the inner shield part simply fits into this groove 312, and a pull-tab 355 formed on the end of the inner shield 294 facilitates this engagement, as well as disengagement, as for cleaning.

As mentioned earlier, the forward part 332 of the flexible inner shield receives a woman's breast within interior space 90, with the nipple projecting to or against the flexible diaphragm 348, and possibly projecting into the narrow channel 349. When a positive pressure fluid is applied to the first pressure port (again, not shown), that pressure is communicated to channel 316 and thence to channel 320, where it will enter a gap 364 between the flexible inner shield part 342 overlying the lip 296. The pressure of the fluid causes the flexible shield part overlying the interior sidewall 293 of the rigid housing 292A to expand or protrude toward the interior space 90, as shown in dashed-lines. The inward flexing of the inner shield 294 is equivalent to applying a massaging and compressive contact to the breast and nipple. It can also be used as a means to "size-to-fit" the shield to a given breast.

As seen above, the flexible diaphragm 334 of the inner shield part 294 and the lid 292B now define an enclosed cavity 330, which is communication with the second pressure port 326. The second pressure port 329 in turn, is in communication with a fluid source (not shown), which is preferably a negative pressure fluid source in this embodiment.

When a negative pressure fluid is communicated into the cavity 330, the flexible diaphragm 348 will be moved toward the lid 292B and out of contact with the nipple of the breast (if it was in contact to begin with). Thus, an intermittent negative pressure will result within the cavity 330, with the flexible diaphragm 348 in turn communicating that negative pressure as a suction force within the interior 90, thereby pulling upon the breast and nipple therein. Some massaging of the nipple and the breast to further facilitate expression of milk can also be effected when the diaphragm returns to its rest position upon release of the vacuum within the cavity. The diaphragm thus serves to separate the source of vacuum (applied to interior 90) from the milk being expressed, as well as anything else that may be carried by the breast (bacteria, etc.). The extracted milk drains through the channel 349 and into the catch chamber 350, where the valve 352 controls the discharge of milk into a collection bottle (not shown) upon a positive pressure (or release of negative pressure) therein, as would be generated when the diaphragm returns to its rest position.

Turning attention to FIG. 10, a seventh embodiment of a breastshield 370 of the invention is shown. In this embodiment, the breastshield 370 comprises an integral, rigid, outer shield part 392 and a flexible inner shield part 394. The rigid outer shield part 392 includes a first portion that is comprised of a hollow cylinder 372 and a second portion that is comprised of a downwardly depending tubular extension 374. The top or forward end 371 of the cylinder 372 includes an outwardly extending lip or flange 376. The bottom end 373 of the cylinder 372 includes an inwardly projecting ridge or flange 378 that extends inboard from the inside wall surface 375 of the hollow cylinder 372 at the point where the first and second portions 372, 374 join. A bottom end 379 of the tubular extension 374 includes a collar 380 for attachment to the collection bottle (not shown). The inside surface 381 of the collar 380 can either be provided with threads 382, some other attachment mechanism for a bottle, such as a snap-fit means (not shown) as would be well known.

Integrally attached to a top area of the breastshield 370 at a point where the first and second portions 372, 374 join together, is a section 385 for connection with pressure sources. As seen in FIG. 10A, this section 385 is provided with internal ports 386, 388 which will provide pressurized fluid to the breastshield. The function of ports 386, 388 will be explained in more detail shortly below, after the description of the inner shield part 394.

The inner shield part 394 is comprised of an upper funnel-like section 390, an intermediate neck 396 and a lower cylindrical section 395. The upper funnel-like section 390 is comprised of a conical part 397 and a tubular part 398 which are integrally joined together. The outer or forward peripheral edge of the conical part 397 is delimited by an inwardly turned edge or rim 400 that snap-fits over the annular lip 376 so as to secure the upper funnel-like section 390 to the hollow cylinder 372 in this region. Likewise, the intermediate neck 396 is provided with the annular U-shaped stirrup 402 which fits over the inboard projecting annular ridge 378 formed on the interior of the outer shield part 392.

The intermediate neck 396 further includes a flexible diaphragm 404 which defines a channel 405 extending through a central portion of the inner shield part 394. The channel 405 is in communication with the interior space 90, which is defined by the area within the interior of the funnel-like section 397 and tubular section 398. The narrow channel 405 is also in direct communication with the catch chamber 407 which defines the lower cylindrical section 395 of the inner shield part 394. The catch chamber 407 includes a valve 409 integrally formed at a bottom of the chamber. The valve 409 has a port 410 for passing expressed milk through the catch chamber 407, and is constructed substantially like the valve presented in the embodiment shown in FIG. 9; therefore no further details of the valve need be provided.

Exterior to the catch chamber 407 is an annular protuberance 412 that is delimited by the small nub 413 which inserts within the annular groove 415 formed into the inside sidewall of the extension 374 above the attachment collar 380. The nub 413 and groove 415 collectively hold the lower cylindrical section 395 of the inner shield part 394 securely within the outer shield part 392 in this area.

When the inner shield part 394 is inserted within the outer shield part 392, an annular first cavity 414 is formed therebetween in the forward part of the breastshield 370, while a second cavity 416 is formed between the diaphragm 404 of the inner shield part 394 and the top end 377 of the extension. As mentioned earlier, the port section 385 is provided with internal ports 386 and 388. It is seen that port 386 is in communication with the first cavity 414 at outlet 418, while port 388 is in communication with second cavity 416 via connecting conduit 389. The second port 388 may be connected to a negative pressure fluid source, while the first port 386 may be connected to a positive pressure fluid source. Alternatively, both can be provided with a negative pressure fluid source. Furthermore, and this will variously apply throughout the embodiments discussed herein, the first cavity may be filled with a gel or a fluid (such as water or air), and the gel or fluid may even be warmed prior to or during use.

When the first cavity 414 is provided with a positive pressure fluid, the upper funnel-like section 397 and tubular part 398 of the flexible inner shield part 394 expands toward the interior space 90, as shown in the dashed lines. Alternatively, if a negative pressure fluid were provided to first cavity 414, this same section would be drawn toward the inside wall surface 375 of the hollow cylinder 372. In either application, a woman's breast received within the interior space 90 will be massaged by the flexing movement of the upper funnel-like section.

The second chamber 416 is provided with a negative pressure, therefore the diaphragm 404 of the inner flexible shield part 394 is drawn toward the inside surface 383 of extension 374, as shown in dashed line form in FIG. 10. This causes a negative pressure (suction) to be conveyed into the interior 90, and as discussed above with respect to the FIG. 9 embodiment, once again serves to isolate the vacuum mechanism from the breastshield. The nipple of the breast may additional be massaged by the diaphragm 404 during flexing, as also discussed above. Expressed milk travels through the narrow channel 404 into the catch chamber 407 before being communicated through the valve 409, and into the containment bottle (not shown) that attaches to collar 380.

FIG. 11 shows an eighth embodiment of the present invention 420 in which the rigid outer shield part 423 has a first portion that is funnel shaped comprising a conical front section 422, integrally connected to the forward end 424 of a cylindrical wall section 430. A rim 421 surrounds the perimeter of the front of the conical section 422. The rearward end 426 of the cylindrical wall section 430 reduces in diameter to form a nozzle or connector section 432. The cylindrical wall section 430 is intersected between its ends by a second portion of the rigid outer shield part, which is comprised of the downwardly angled tubular section 434. The connector section 432 terminates with an annular pump collar 436 which connects the breastshield to a fluid source which can provide both positive and negative pressures.

The outer shield part 423 further includes the internal partition wall 438 which extends from the forward end 424 of the cylindrical section 430, to the annular pump collar 436. The internal partition wall 438 further has a wall 440 that is generally centered within the interior of the downwardly angled tubular section 434, and serves as a splash wall to keep expressed milk from passing up a channel 448 further defined within the outer shield part 423. There is a stub wall 442 at the forward end of the cylindrical section 430, and with the internal partition wall 438 define a first pressure channel 444, which has an outlet 445 that communicates with an internal space 446 defined between the inner shield part 447 and the adjacent interior sidewall of the outer shield part. As noted above, the separation wall 440 with the adjacent interior sidewall of tubular section 434, defines a second pressure channel 448. The first and second pressure channels 444, 448 commonly terminate at the collar 436 of nozzle section 432.

The inner flexible shield part 447 is also generally funnel-shaped, having a front conical part 450 that is complementary to, and received within the front conical section 422 of the outer shield part 423. The inner shield part 447 also has a tubular part 451 received within the cylindrical section 430 of the outer shield part 423. The conical section 450 and tubular part 451 define the interior space 90 for receiving a woman's breast therein.

The conical part 450 includes an annular groove 454 which snap-fits over the rim 421, thereby securing the inner shield part 447 to the outer shield part 423 at the front end of the breastshield. The tubular part 451 has a first end integrally joined to conical part 450 and a floating (unanchored) second end 456 that terminates at the location upstream of the splash wall 440. A woman's breast would be received within the part of the interior space 90, with the nipple extending into the tubular part 451.

The tubular part 451 has a wall thickness which may be formed so that it reverse tapers, meaning that it increases in radial cross-sectional thickness from the front end to the rearward end, indicated at 456. The tapered wall thickness forms an annular tapering space 457 between the inner surface 435 of the cylindrical section 430 of the outer shield part and tubular part 450 of the inner shield part. The tapering annular space 457 is in communication with the chamber 446 and with an exhaust (vent) port 458 located near end 456 of the inner shield part. The exhaust port 458 releases to the surrounding atmosphere, as will be explained below.

In operation, the annular pump collar 436 connects to a dual fluid pressure source (not shown), such that the first pressure channel 444 communicates a positive pressure fluid through the channel into the chamber 446 before entering the tapering space 457. The initial positive pressure build-up of the fluid entering the tapering space 457, first contacts the thinnest part of the tapered wall of the tubular part 451, forcing an expansion of the wall inwardly toward the interior space 90. This is intended to form a moving wave along the tubular part 451 from front to rear. A rapid intermittent discontinuous positive pressure fluid applied to the tapering space 457 creates one rolling wave or a series of rolling wave configurations formed by each succeeding, intermittent burst of pressurized fluid, as indicated in dotted line fashion in FIG. 11. Because the wall thickness of the tubular part 451 of the inner shield 447 increases toward the rearward end 456, the series of toroidal waves gradually reduces in size (height). Because the fluid source is intermittently supplied, the degree of inward wall expansion along the taper decreases in a cascading, or rippling manner. The positive pressure is released at the second end 456 through the exhaust port 458 to the surrounding atmosphere.

A negative pressure fluid source (not shown) connected to the pump collar 436 communicates a negative pressure or vacuum in the second pressure channel 448, which is communicated around separation wall 440, into the interior space 90. The negative pressure cyclically pulls upon a breast. Extracted milk drains into a collection bottle (not shown) received on the bottom end of the downwardly angled tubular section 434 in manner already described above.

Turning attention to FIG. 12, a ninth embodiment 460 of a breastshield of the invention is shown. In this embodiment, rigid outer shield part 461 has two parts, one of which is a mounting base 463 which includes a base plate 464, while the forward end 465 of mounting base 463 includes an offset U-shaped ring 474. An angled tubular extension 467 intersects with a conduit 462 defined by the sidewall 472 (which yields a short cylinder). The tubular extension 467 has a bottom end 470 which includes a flange 471 surrounding the end 470. There is a downwardly depending separation wall 483 that projects into the interior 468 of tubular extension 467, and serves as a splash wall, as previously described with respect to the FIG. 11 embodiment, for one example.

The U-shaped ring 474 includes an outermost wall 480 having a threaded inside surface 482 that receives the other part of this rigid outer shield of FIG. 12, which is an articulating part 490. The closed base of the part 490 at 487 fits within the ring 474 in a screw fit, via matching threads 473.

The articulating part 490 in effect comprises a bladder-like structure. It has a generally double-walled frustoconical shape which defines the interior space 90 for receiving a woman's breast therein along its inboard sidewall 488. The outside sidewall 491 of the part 490 smoothly joins with the inboard sidewall 488 along the front or forward rounded end 500. The articulating part 490 can be formed of substantially rigid plastic material, and formed as an integral whole. As will be evident, the articulating part 490 defines and internal chamber 499 which is closed, except at a port 498.

The articulating part further includes an outboard opening major V-shaped channel 492, and the inside sidewall 488 includes two inboard opening laterally spaced minor V-shaped channels 494, 496, one on either side of the major channel (along the longitudinal axis). These major and minor channels extend around the perimeter of the articulating part. The pressure port 498 communicates a source of positive pressure fluid into the interior cavity 499. This could be, for instance, warm water, a liquid gel, or the like, and not just air.

A flexible inner shield part 485 is seen to encase the articulating part 490 wherein an upper portion 502 of the inner shield part 485 is folded over the top, rounded edge 500 of the front end of the articulating part. The elastic nature of the inner shield part 485 securely holds the inner shield part in place against the inside surface of the sidewall 488. The flexible inner shield part 485 is formed to generally conform to the frustoconical shape of the articulating part, and has a downstream end 486. The downstream end is shown to overlap the inboard side of the U-shaped ring 474.

In use, a negative pressure fluid source (not shown) is attached to the base plate 464 of the rigid outer shield at conduit 462, thereby conducting a vacuum through the channel between splash wall 483 and the adjacent sidewall of the tubular extension 467 into the interior space 90. A positive pressure fluid source, for example, is provided through port 498 into interior cavity 499 of the articulating part 490. The major channel 492 acts as a hinge, thereby flexing the front end 500 of the articulating part 490 outwardly as shown in the dotted lines. The minor channels 494, 496 facilitate the flexing of the bladder-like structure about the major channel by providing some expansion of the sidewall. Intermittent positive pressure in the articulating part's inner chamber 499 yields a cyclic flexing movement of the articulating part 490 and hence inner shield part 485, which will perform a cyclic massaging effect upon the breast which is received in the interior space 90, thereby promoting milk to be expressed from the breast. In a similar manner, negative pressure at 462 could be used to generate the cyclic flexing movement. The milk is then communicated under vacuum toward the separation wall 483 and then downward through the tubular member 467, where it is collected in a bottle (not shown) connected to flange 471, as is well known. In an alternative modification, a pressure source could be connected with the minor channels 494, 496. If this were a positive pressure source, for example, the chambers formed between the minor channels 494, 496 and the flexible inner shield 485 overlying those channels, would be caused to expand. This would likewise result in an outward flexing of the front end 500 at the hinge formed by the major channel 492. A negative pressure applied to these channels/chambers would cause an inward bending.

FIG. 13 shows a tenth embodiment 505 of the breastshield of the present invention. In this embodiment, which is similar to that of the FIG. 12 embodiment, there is an outer shield made up of two parts, one of which is a base part 506 which has a downwardly angled tubular member 598. The bottom end 600 of the tubular member 598 is provided with a flange 602 that connects to a bottle using an intermediate collar member (not shown) as is well known.

A front end 508 of the base part 506 is defined by a sidewall 514 the inside surface 515 of which is threaded to receive the other part 550 of the outer shield which will be described shortly hereafter. An interior shoulder is provided at 516. Between the sidewall 514 and the shoulder 516 is received an annular removable U-shaped collar 525, which functions as a fluid communication member. The collar 525 is comprised of an annular base member 527 resting on shoulder 516 and an inboard upwardly projecting ring 529 spaced from the interior of wall 514.

A central chamber or passageway 531 is formed inboard of the other part 550 of the outer shield, in combination with a flexible inner shield part 570. An undercut 533 along the bottom (or rearward) surface of the annular collar 525 forms a conduit or passageway for fluid (air) flow through an outlet 521 formed in a port 522, as will shortly be described, as will how this communication is completed in combination with additional structure of the flexible inner shield part 570 in the vicinity.

The base part 506 of the outer shield also includes a port 518, which ends in an offset undercut 520, thereby forming an outlet for port 518. It will be seen that this outlet is annular in this embodiment, extending into widened channel part 544 in the tubular member 598. This outlet/channel for port 518 is in fluid communication with an annular channel 535 which is formed in the bottom (rear) of the removable collar 525 when the latter is received within the base part 506. Channel 535 has one or more internal conduits in the form of throughbores 536 which open into another annular channel 537 on a forward side of the collar 525.

Completing the outer shield part of the breast receptacle of this embodiment of FIG. 13 is the double-walled member 550, which here is formed of a semi-rigid material having the ability to flex, as will be shortly evident. The member 550 is defined by the outer sidewall 552, the inner sidewall 554, the top smooth transitional surface 556, and the rearward annular threaded neck 558, which further includes the planer base surface 560. The planer base surface 560 includes the intake opening 562 that is in communication with the channel 537 of the removable collar 525. Thus, an internal chamber 564 is defined within the sidewalls of the member 550 which is in fluid communication with the passageway 518 formed in the base part 506.

The breastshield further includes the inner flexible shield part 570 that is disposed within the member 550. The inner shield part 570 comprises a widened top (or forward) end 577 which extends into a constricted stem 582. The upper end 577 has an outwardly and then downwardly projecting curved section 580. As illustrated in FIG. 13, the curved section 580 hooks (snap-fits) around the top transitional surface 556 of the outer shield member 550, thereby securing the inner shield part to the outer shield part in this front area of the breastshield.

A disk-shaped base 590 is integrally formed as the bottom end of the stem 582. It has a bottom surface 592 resting on another shoulder 523 formed in the base part 506. The distance between the undercut 533 formed in the bottom surface of the removable collar 525 and the top surface 594 of the base member 590 is such that the lower end of the inner shield part is effectively seated on the shoulder 523 at rest, and also under a positive (or negative) pressure within the chamber 531, and/or a negative pressure within the tubular member 598 as applied at 604. The lateral (radial) dimension of the disk 590 is likewise chosen to yield the passageway 533 leading to the port 522.

As FIG. 13 further illustrates, inner sidewall 554 with its overlying flexible shield material form an interior space 90 for receiving a woman's breast therein. An internal space 588 is further defined by the flexible shield along the stem 582, which ends in an opening 595 in the disk 590. That opening 595 is in fluid communication with the interior 604 of the tubular part 598. It will be noted that a ring-like pull 596 is formed on the disk, which facilitates the mounting of the flexible shield part within the outer shield part. That is, the outer shield part 550 would be assembled with the collar 525. Flexible shield part 570 would then be mounted to the outer shield part 550, with the stem 582 pulled through the collar via pull 596. This united assembly would then be screw-threaded to the base part 506.

The nipple of a woman's breast may be received at the very front of the internal area 588 at the top end of the stem 582; it need not reach that far, however. As noted, area 588 is in fluid communication with the interior space 90 on one end thereof, and with the interior 604 on its bottom end 579. In operation, a positive pressure fluid source (not shown) and a negative pressure fluid source (not shown) are respectively connected to and in communication with the port 518 (positive) and the port 522 (negative) of the outer shield part. The positive pressure via port 518 is communicated through opening 562 such that the internal chamber 564 of the member 550 is filled with a positive pressure fluid and expands. The filling of internal chamber 564 will cause the sidewall 554 to slightly flex into the interior space 90.

The negative pressure via port 522 communicates with the interior chamber 531 formed of the combination of the outer shield inner sidewall 554 and its adjacent inner shield sidewall defining the stem 582. This will cause the chamber 531 to contract, widening area 588. This in turn communicates a negative pressure (suction) within interior space 90, which serves to pull upon the breast and nipple. When the negative pressure is released on chamber 531, the chamber returns to its rest position, potentially constricting or gently squeezing the breast/nipple therein. Likewise, release of the positive pressure to chamber 564 returns the forward part of the breast receptacle to its rest position. This movement of the forward and rearward segments of the breast receptacle will cause a massaging and manipulation of the breast and nipple, which can be timed in a desired manner.

An eleventh embodiment 610 of the invention is illustrated in FIG. 14. In this embodiment, the outer shield part is once again comprised of two sections; a rigid base section 611 and a removable rigid forward section 638. The base section 611 has a downwardly angled tubular member 612 having a forward portion 613 that terminates in an annular U-shaped ring 614 that defines a U-shaped channel 615. A rearward portion 624 terminates with an annular attachment collar 625 having internal threads 626 for securing to a milk collection bottle (not shown).

A conduit or port 635 is defined by a cylindrical sidewall structure 628 that has one end terminating in an outlet 629. The other end of the port 635 opens into pump collar 632. The pump collar 632 includes internal threads 633 for connection to a breastpump, such as a manual breastpump (not shown) as is well known.

The U-shaped ring 614 is comprised of an outer wall 616, an inner wall 620, and an interconnecting base wall 619 (through which outlet 629 is defined in one area). The outer wall 616 has a smooth interior surface 618, while the inner wall 620 presents a planar angled surface 622.

The forward section 638 of the outer shield is comprised of a rigid barrel-shaped part defined by sidewall 639 having a rearward end 640 that press-fits with the interior surface 618 of the outer wall 616 of the U-shaped ring 614. The barrel part 639 is integrally joined to a bowl or conical section 644 at area 642. The point of transition between the part 639 and the conical section 644 forms an inwardly projecting protuberance 646, which defines an exterior (outboard) facing annular groove 648. The forward end of the bowl section has a peripheral edge surface 653.

The breastshield 610 also includes a flexible inner shield part 656 received within the outer shield part. The inner shield part 656 is comprised of a cylindrical section defined by sidewall 674, which is in a spaced relationship from the barrel-defining sidewall 639, thereby forming a cavity or chamber 670. A rearward end 658 of the cylindrical section sidewall 674 is formed with a base ledge 662 that is received inside the U-shaped channel 615. The base ledge 662 has an angled wall 664 that is frictionally fitted against the angled inner wall 620 of the U-shaped ring 614 and against the inner surface of sidewall 639. A port 637 is formed as a throughbore in the base ledge 662. The forward end 660 of the cylindrical section defined by the sidewall 674 of the inner shield part 656 is provided with a groove 665 that is received over the inward protuberance 646. This forms a firm fit, and positions the inner shield part 656 in this area. The cylindrical section of the inner shield part 656 defines the interior space 90 which is in communication with the interior 672 of the downwardly angled tubular member 612. A funnel section 667 of the inner shield part 656 is in close contact against the inner surface of the bowl section 644. The funnel section 667 has a forward end 668 that terminates with an outwardly extending lip 669 which is received over the peripheral edge surface 653 of the bowl section 644 for securing the inner shield part 656 at this area.

The outboard facing surface of sidewall 674 of inner flexible shield part 656 also includes an outboard extending bead 678 extending around its perimeter, which is laterally spaced from another bead 680. The function of the beads is explained below. The funnel section 667 of the inner shield part also forms a part of the interior space 90 that receives the woman's breast. The nipple of the breast, when received within the funnel section 667, extends beyond the annular protuberance 646.

In operation, a vacuum source (not shown) is connected to the pump collar 632, or via tubing to the port 635, to communicate a negative pressure fluid into the chamber 670. The first and second beads 678, 680 function as sequential shut offs. The negative pressure first applied to the cavity 670 will cause the inner flexible shield part along sidewall 674 to be drawn toward the rigid outer shield sidewall 639. This is shown in the figure in dashed-lines, where the first bead 678 will contact the inner surface of sidewall 639. As the vacuum builds, the second bead 680 will then contact the inner surface of sidewall 639. This will result in a gradual expansion of the inner chamber 90 extending from front to rear of the breast receptacle. This can be done intermittently, with release of the negative pressure or alternatively with application of a positive pressure to thereby expand the chamber 670 and also compress the breast/nipple therein.

A twelfth embodiment 702 made in accordance with the invention is presented in FIG. 15. As seen, the outer rigid shield part is configured like a funnel, having a conical section 686 integrally connected to a cylindrical section 696, which ends in a base part 708 which is generally tubular in shape. The first end 688 of the conical section is delimited by the upstanding rim or lip 692. The bottom end 710 of the angled tubular member 708 includes a ring 712 for attaching it to a milk collection bottle via a collar (not shown) as is well known. The interior of the tubular section is indicated at 714, and has a downwardly depending separation or splash wall 716 which is attached to the interior surface of sidewall 707. Sidewall 707 further defines a pressure channel or port 706. As in previous embodiments, tubular section interior 714 would be in communication with a negative pressure source (not shown) via port 706.

The cylindrical section defined by sidewall 696 also includes an internal annular ledge 700 that is formed in the inner sidewall surface 698. The ledge 700 receives the holder member 726 therein. The holder member 726 comprises an internal sidewall 728 which has a bottom end 729 that is received on the internal annular ledge 700, and an external short wall 730 that includes an outboard extending peripheral rim or shelf 732, which is in resting contact against the end surface 694 of the lip 692. The bottom end 734 of the short wall 730 extends inside the conical section 686 to a shoulder 689. Between the walls 728 and 730 extends an annular well 738.

Received within the well 738 is a doughnut shaped or toroidal gel pack 740 (or containing air, or water, or foam, etc.). The toroidal gel pack 740 is held within the well by the inner flexible shield part 735, as will be shortly described.

The inner flexible shield part 735 is comprised of an interior sidewall 741 which extends into a curved part 742 and ends in an exterior wall part 743. The flexible shield part 735 would be made as an integral whole. It will be noted that the interior sidewall slightly increases in wall thickness as one moves from rear to front. The curved part 742 forms the opening to the breast receptacle. The flexible shield part 735 fits over the combined holder member 726 and rigid outer shield part, with the gel pack 740 held within the well 738.

Once again, the inner flexible shield part defines the interior space 90 which receives a woman's breast therein. The interior space 90 is in fluid communication with negative pressure via port 706. It will be noted that the rear (downstream) end of the inner flexible shield part seals against the inside surface of the sidewall 696.

The holder member 726 is here shown as a rigid piece. It might, however, be formed of a semiflexible material which is rigid enough to support its shape and position the gel pack, but flexible enough, at least along its inboard sidewall 728, to allow some movement under pressure. That pressure would be applied within the chamber 725 defined between the combined holder member 726 and the conical section 686 of the rigid outer part. That pressure could be a positive or negative pressure, as desired, and applied through a port (not shown) through the sidewall 686.

Pressure, such as a positive pressure, is likewise provided in the cavity within which the gel pack is located, or to the gel pack itself. With the flexible shield part suitably anchored at its ends, and the walls of the flexible member suitably thinned in the curved region 742, the gel pack section could be made to expand and contract, as shown in dotted line fashion. The advantage of the gel pack 740 over a simple hollow chamber is that the gel pack could be made warm or cold, adding this additional therapeutic effect of temperature variation to the breastshield.

A thirteenth embodiment 750 of the invention is presented in FIG. 16. The outer shield part is once again comprised of two rigid pieces. One is the base 758 that has a downwardly angled tubular member 759. The bottom end 760 of the downwardly angled tubular member 759 includes the annular attachment collar 762 which is internally threaded 763 for attachment to a milk collection bottle (not shown) as is well known. At the forward end of the base part 758 is a stub cylinder part 752. There is also a port 770 defined in the base 758 by interior sidewall 766 and external sidewall 767. That port 770 has an outlet at 768. The forward outboard side of sidewall 767, indicated at 769, is externally threaded in conjunction with a sidewall 785 spaced inwardly from the stub cylinder part 752, the sidewalls 769, 785 together forming a continuous attachment collar. This collar receives the other piece of the rigid outer shield part, in the form of a generally cylindrical cup 788. Cup 788 has a threaded connection with the annular collar of the base rigid outer part at its rearward end 790.

Mounted to the cup 788 and the base 758 of the rigid outer shield part is flexible interior member 784. The internal structure of the interior member 784 will be described in more detail momentarily. In general, however, it has a perimetrical edge 795 which is fixed to a rigid coupling ring 800. Coupling ring 800 has an external bead 804 which is received in a complimentary shaped groove 796 formed in the cup 788 at its forward end. This connection serves to position and mount the flexible interior member 784 at the forward end of the breast receptacle. The rearward (downstream) end of the flexible shield part 784 terminates in a collar-like structure 765, which fits over the outside of the stub cylinder 752. There is a flange or rim 771 extending from the opening of the collar structure 765, which abuts against an inboard extending flange 772 of the cup 788 at this end. This serves to further fix and position the flexible shield part.

A double-walled structure is provided for the flexible shield part in this embodiment of FIG. 16. However, rather than defining a single chamber to be subjected to positive/negative pressure therebetween, this flexible shield part is uniquely formed into a tri-part member that is also best seen and understood from viewing FIG. 16A. The inner shield part 784 is formed by three separate inner sidewalls 780, 782, 785, which collectively form a unitary inner shield part. The space between the inner surface 798 of the sidewall 788 and the interior surfaces of each inner sidewall 780, 782, and 785 form three chambers, which can be in communication with each other or can be completely separate chambers 806, 808 and 810. If so separate, then additional ports to that of port 770 could be provided, to allow independent pressure adjustment of each chamber.

In a rest state, i.e., the chambers 806, 808 and 810 not under negative pressure for instance, the breast receptacle presented by tri-part inner flexible shield part 784 will be as shown in FIGS. 16 and 16A. This will be a short conical front part extending into a restricted stem part 812. The interior space 90 is thus initially so defined. The stem passage 812 is in fluid communication with the interior 815 of the tubular member 758.

In operation, a negative pressure fluid source is connected to the pressure port 770, and thereby communicating with the three chambers 806, 808 and 810 that are formed by the inner flexible shield part 784 in combination with the outer rigid member 788. Intermittent application of the negative pressure source will cause a cyclic collapsing and expansion of the three chambers, simulating a baby's sucking action on a woman's nipple, thereby promoting increased milk extraction. As is evident, the negative pressure thus generated is communicated to the stem 812 and remainder of the interior 90, pulling upon the breast and nipple therein. The extracted milk flows through passage 812 into the interior 815 of the angled tubular member 758 and to a collection bottle (not shown) attached to the attachment collar 762. It will be understood that operating this embodiment with independently pressurized and controlled chambers 806, 808 and 810 opens up further possibilities for a desired manipulating of the breast and nipple, such as through a movement that seems to rotate around the axis of the breast receptacle.

A fourteenth embodiment 817 of the breastshield of the invention is shown in FIG. 17, and is similar to that of the preceding FIG. 16. The outer shield part is a two-piece rigid structure, having a base part 822 and a cup-shaped piece 875. There is an integrally attached pump collar 824 that includes threads 825 for removable connection to a breast-pump (not shown). The forward end of the base part 822 has an integrally formed U-shaped ring 830 that includes an outside wall 832, an inside wall 828 and the interconnecting base wall 826, which collectively define the U-shaped channel. The outside wall 832 has a threaded interior surface 831 for attachment of the cup piece 875, in a manner to be hereafter described.

A port 852 is formed in the base part 822, with an outlet that opens into the base wall 826 of the U-shaped channel at at least one point 853. A positive or negative fluid source may be attached to the pressure port 852 and conveyed into the U-shaped ring or channel 830, as will be explained later herein.

The rigid outer shield base part also includes a downwardly angled tubular member 855. The tubular member 855 has a bottom end which terminates in a short extension 865. The extension 865 would have a valve assembly attached thereto, such as shown in U.S. Pat. No. 4,929,229. Of course, such a valve assembly would likewise be used with other embodiments discussed herein. There is an attachment collar 866 which includes internal threads 867 for attachment to a bottle (not shown). The interior of the tubular member is indicated at 857.

Cup piece 875 is formed of sidewall 872. Its rearward end includes the externally threaded portion 874, for threaded engagement within the threaded interior surface of wall 832 of the U-shaped ring. The forward end of the cup piece 875 has a groove 878 formed in the inner surface of the sidewall 872 for receiving a bead 880 projecting from an inside surface of a rigid ring-shaped coupler member 884. The rigid coupler member 884 is preferably made of a plastic material of a type that is either the same or equivalent as that of the outer shield cup piece, and is permanently attached to the inner flexible shield part 886.

The flexible inner shield part 886 is comprised of a unitary wall member that, from the coupler member 884, extends into a forward curved potion 892 and then into interior sidewall 898. A second rigid ring-shaped coupler 890 is attached at the rearward (downstream) end of the sidewall 898. Rigid coupler member 890 is received within the U-shaped channel of the base part, contacting against the inboard surface of the sidewall 828 in a sliding engagement. Rigid coupler member 890 is spaced from the cup piece sidewall 872 within the U-shaped channel of the base part, thereby leaving a space in communication with the outlet 853. That space opens into a cavity or chamber 833 defined between the cup piece sidewall 872 and the flexible inner shield part 886. Sidewall 898 of the flexible inner shield part 886 once again defines the interior space 90, which receives the woman's breast and nipple therein.

The breastshield 817 further includes a flexible diaphragm 910. The diaphragm has a front end 912 with sidewall structure 913 that forms a cylinder that is closed at this front end 912. It will be noted that there is a slightly indented portion 914 of this cylinder, which overlies the area leading into the top (upstream) end of the tubular portion 855 of the base part. This serves to allow milk to pass into the tubular portion 855, as will be shortly evident. The rearward end of the diaphragm includes a flange-like extension 917 that serves to seat the diaphragm against the forward end of the collar 824. An interior space to the diaphragm is indicated at 919.

Before turning to the operation of this embodiment of FIG. 17, it is seen that the flexible inner shield part 886 has an undulating inboard facing surface. This is formed of circumferential thickened areas 897, which form a hill-and-valley structure along the interior 90.

In operation, a positive and/or a negative fluid source is connected to the port 852 (as through a connection not shown, but readily understood). A negative (suction) pressure is connected at pump collar 824 in the usual manner. The negative pressure applied to the interior 919 of the diaphragm is intermittent, and causes a cyclic collapsing and expansion of the diaphragm 910, creating a vacuum within interior space 90, which acts upon a breast and nipple therein. The diaphragm thus serves to isolate the vacuum source applied at the collar 824 from the milk supply. Further detail of this type of diaphragm and its operation can be gleaned from U.S. Pat. No. 5,941,847. The milk flows under the indented portion 914, into the tubular section 855 and thence to a collection bottle.

The positive and/or negative pressure communicated to pressure port 852 causes the chamber 833 to expand or contract in volume. This in turn causes the inner flexible shield part sidewall 898 to move inwardly or outwardly relative to the breast/nipple in the interior space 90. The flexing action forces the ridges 897 into contact against a breast and nipple, thereby massaging the breast to facilitate milk expression.

Figure 19:
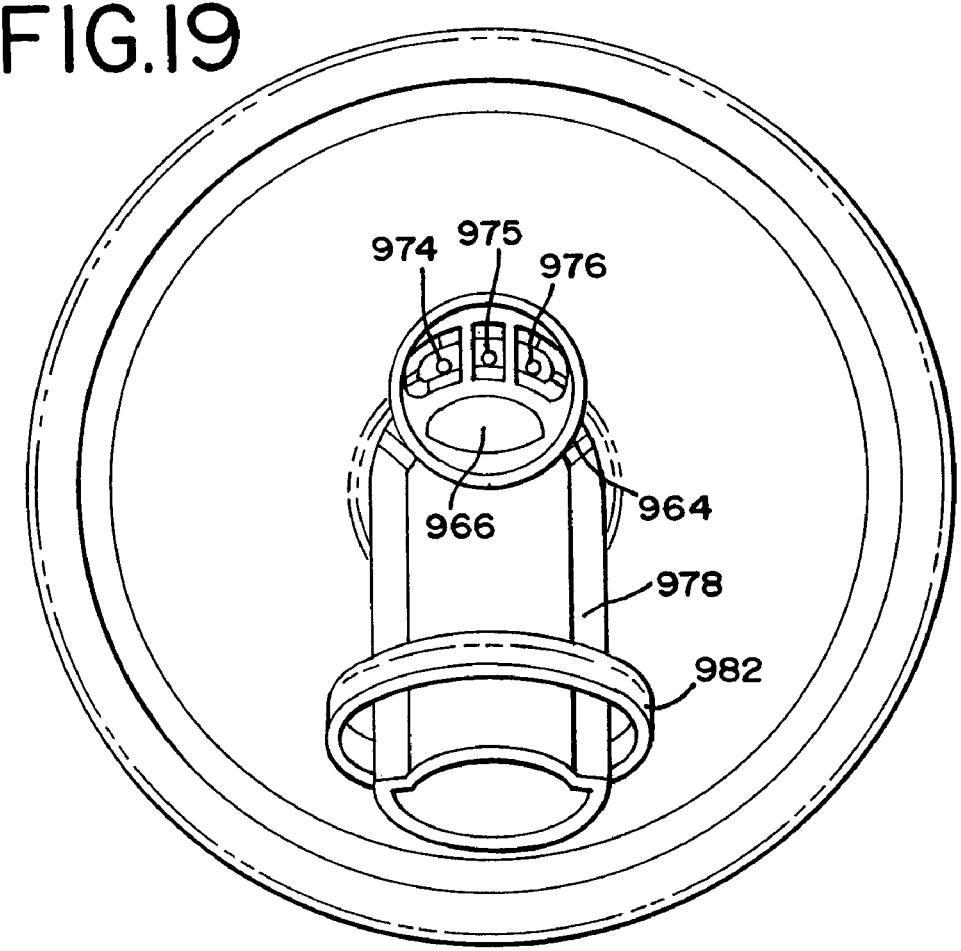
FIG. 19 is a reduced-sized rear view of the breastshield of FIG. 18.

A fifteenth embodiment 950 made in accordance with the present invention is shown in FIGS. 18, 19, and 19A. The breastshield 950 of this embodiment has a single piece rigid outer shield part which is comprised of a funnel section 952, a cylindrical section 956, and a tubular member 978. The periphery of the funnel section 952 is comprised of a flange or rim 954. The cylindrical section 956 and tubular member both communicate with a barrel section 962 which is also formed integrally with the foregoing, and will be described in more detail below. The angled tubular member 978 has a bottom end 980 that includes an attachment ring 982, all as is well known for attaching a milk collection bottle thereto with an attachment collar (not shown). The angled tubular member 978 further includes a separation or splash wall 984 that defines a vacuum passage 986 within the tubular member 978, and the interior of the tubular member is generally indicate at 988.

The barrel section 962 includes a pump collar 964 for attachment to a pump, which is intended to be an electrically driven breastpump, but could also be a manual (e.g., hand reciprocated piston-type) pump. The pump collar 964 delimits two passageways or ports; one is port 968, the other is port 966. Port 966 communicates with the vacuum passage 986 via an outlet 990. The forward end of the port/passageway 968 ends in an outlet 972.

With reference to FIG. 19, it will be seen that port 968 actually includes three pressure ports/passageways 974, 975, and 976 formed within the barrel section 962. The nature of these ports/passageways will soon be made clear.

Also forming the breastshield 950 of this embodiment is the flexible inner shield part 993, which in this version is frictionally inserted within the rigid outer shield part. The flexible inner shield part 993 is comprised of a flexible conical member 992 and a tubular extension 996, which together define the interior space 90. The forward end of the conical member 992 has a peripheral edge that is delimited by the annular rim 998 that has a downwardly extending lip 999. The rim 998 is received on the flange 954 to fix and position the flexible inner shield part around the front of the breastshield. As seen in FIG. 18, the tubular extension 996 terminates at a rearward point which is sized to abut against the interior surface of the sidewalls 957 and 958 which define the rigid outer shield part in this area. This frictional engagement is intended to be sufficient to fix and position the tubular extension 996 in this area.

As best seen in FIGS. 19A, 21 and 22, the inner shield part also includes a distribution manifold member 1000 integrally formed into the tubular extension. The distribution manifold member 1000 includes a first 1002, second 1004, and third 1006 channel which communicate with the preformed first annular channel 1008, the second annular channel 1010 and the third annular channel 1012. Each channel 1008, 1010 and 1012 has a thinner wall thickness than the remainder of the inner shield part (see FIG. 18). The wall thickness and shape of the channels 1008, 1010 and 1012 have a functional aspect that will be described in the operation of this embodiment. As best seen in FIG. 18, for instance, the first and second annular channels 1008, 1010 are longitudinally spaced from each other and disposed along the tubular extension 996, while the third channel 1012 is formed within the conical member 992.

Each annular channel forms a respective annular air chamber 1014, 1016, and 1018 when the inner and outer shield components are combined. As best seen in FIG. 18, when the inner shield part is inserted into the outer shield part, the distribution member manifold member 1000 is connected to the pressure ports 974, 975 and 976 via respective first, second, and third, passageways 1006, 1004 and 1002.

In operation, a negative pressure fluid source (not shown) is connected to the pump collar 964, where a vacuum is communicated into interior chamber 966, which in turn, communicates the vacuum through outlet 990 and ultimately into interior space 90. A negative and/or positive pressure fluid source is also communicated to the port 968. This could be a single source which will operate on the three chambers 1014, 1016 and 1018 simultaneously, or a plurality of pressure sources each being connected to a respective port 974, 975 and 976. It will be understood throughout this disclosure that such a plurality of pressure sources could be obtained from a single source of vacuum/positive pressure, with the pressure split, as well as independently controlled, as desired. Assuming that a vacuum is provided through the first, second and third inlet pressure ports 974, 975 and 976, the vacuum is then communicated through the respective first, second, and third passageways 1002, 1004 and 1006 of the distribution manifold 1000 (See FIG. 19A), which in turn, draws vacuum in the chambers 1014, 1016 and 1018.

Vacuum will pull the thin-walled preformed annular channels to the position shown in dashed lines, i.e., outboard. An intermittent vacuum applied (with release of the vacuum) will therefore cause a cyclic flexing of the sidewalls defining the chambers 1014, 1016 and 1018. A woman's breast received within the interior space 90 is massaged by the flexing action of the third annular air chamber 1018, while the nipple is massaged by flexing of the first and second annular air chambers 1014, 1016. With independent control of the pressure to each chamber, a wide variety of patterns can be obtained for the sequence of the operation of the chambers, as well as the amount of tactile sensation for the sidewalls of these chambers to be making with the adjacent breast or nipple through control of the positive pressure exerted by the sidewalls against the breast and nipple.

In FIG. 20 a sixteenth embodiment 1020 of the breastshield of the present invention is shown. This embodiment is very similar to the previously presented embodiment of FIGS. 18, 19, 19A, 21 and 22, therefore the description of the rigid outer shield part will not be provided because it is structurally the same as the one just described (like numbers, once again, designate like parts). There are some structural differences between the previous inner shield part and the present one, however.

In this embodiment 1020, the inner shield part is provided with annular first, second and third air ducts 1022, 1024, 1026, instead of the somewhat bulbous inwardly extending annular preformed channels of the previous embodiment. Each air duct is formed by providing a rectangular cross-section annular cavity within the side wall forming the inner shield part, in approximately the same relative locations as the previously described annular channels 1008, 1010 and 1012. The actual cross-sectional cavity is not very significant, however. The ducts are formed so as to thin the sidewall 1028 of the flexible inner shield part over the ducts, thus leaving a wall cross sectional thickness indicated at 1030 in the duct area that is thinner than the normal thickness indicated at 1032 at the locations shown in FIG. 20. The location of each air duct corresponds with the location of the annular channels 1008, 1010 and 1012 provided in the previous embodiment.

The FIG. 20 embodiment functions in the same manner as the previously described embodiment, except now a positive pressure fluid source(s) is intended to be applied to the ducts 1022, 1024 and 1026. This will result in a bowing inboardly (i.e., into the interior area 90) of the sidewall over the ducts, creating annular ridges as indicated in dotted line fashion in FIG. 20. Once again, an intermittent supply of a positive pressure fluid, which may be further modulated and controlled in timing and amount, creates a cyclical flexing toward and away from the interior space 90, thereby performing a massaging effect.

Turning attention to FIG. 23, a seventeenth embodiment 1035 of the breastshield of the present invention will be described. As illustrated in FIG. 23, the rigid outer shield part comprises a conical front section 1036 integrally joined to a cylindrical section 1045, with an inside wall surface indicated at 1042. The front end of the conical section 1036 ends in a smooth lip or rim 1041.

The flexible inner shield part in this embodiment of FIG. 23 (only one side in cross-section is depicted) is comprised of a conical part 1055 and a tubular part 1056 which collectively define the interior space 90. The conical part 1055 receives the woman's breast while the tubular part 1056 receives the nipple. The front end of the conical part 1055 is seen to terminate in a somewhat thickened beadlike perimeter 1060. This perimetrical bead rests against the rim 1041 of the underlying rigid conical section 1036. The other or downstream end of the tubular part 1056 is loosely received in the cylindrical section 1045.

An outlet 1066 is formed through the wall defining the conical part 1055 of the flexible shield part, and is seen to extend into a channel 1067 defined between the perimetrical bead 1060 and another circumferential bead 1068 formed radially inboard and concentric therewith. As seen in the illustration, when the flexible inner shield part is inserted within the rigid outer shield part, a space 1070 is formed therebetween along substantially the whole length of the flexible shield part, except at the interface between rim 1041 and bead 1060.

Along the internal sidewall of the tubular part 1056 are formed circumferential ridges 1072, which are intended to contact the nipple.

Operationally, it is anticipated that a negative pressure fluid source (not shown) be provided through any of the means previously disclosed herein or otherwise known, such that both the interior space 90 and the space 1070 would be under vacuum. A woman's breast received within the interior space 90 would experience suction. The negative pressure would also extend into the space 1070, creating a seal around the breast at the channel 1067. The negative pressure provided within the space 1070 in conjunction with the suction on the breast will also cause the tubular part 1056 of the inner flexible shield part to be drawn toward the vacuum source, or in a direction axially away from the breast of the user. The drawing shows this in dotted line fashion, with the end 1073 of the tubular extension moving as indicated. The protrusions or ridges 1072 that are provided within the tubular part 1056 on the inside surface of the inner shield likewise move to the same elongated position, drawing upon the nipple, in what may be characterized as a "Chinese finger grip effect".

Figure 25:
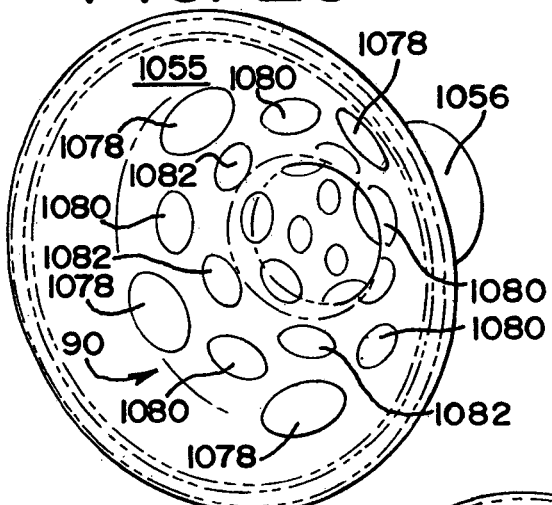
FIG. 25 is a perspective view of an adaptation of an inner shield part made in accordance with an aspect of the present invention.

Moving on to FIGS. 25 and 24B, 24C, in FIG. 25, variations on the theme of the FIG. 23 embodiment are shown. One takes the form of a series of randomly located solid, or alternatively air bubble type, protrusions that may be provided throughout the conical part 1055 and on the tubular part 1056 of the inner flexible shield part. In this embodiment, the protrusions may have an oval shape and the physical size of each protrusion may vary so that a first series of large oval-shaped protrusions 1078 are presented along a same radial plane. Disposed in between the locations of the large oval protrusions 1078 is a midrange size of oval-shaped protrusions 1080, each of which is also presented along a respective same radial plane. Likewise, the protrusions may progressively become smaller (1082) and be presented along a series of radial planes sequentially extending from the conical part 1055 to and into the tubular part 1056. As mentioned earlier, the space 1070 between the flexible inner shield part and the rigid outer shield part is provided with negative pressure which causes the inner shield part to longitudinally extend or stretch. Thus, it can be appreciated that dependent upon the shape, arrangement, and location of the projections, and whether the projections are solid or in air bubble form, a slightly different massaging effect upon a breast and nipple disposed within the interior space will be experienced. The adaptation of these projections to other embodiments herein will be understood.

FIG. 24C shows an air bubble type structure. FIG. 24B utilizes solid projections, indicated at 1078' and 1080'.

Figure 26:
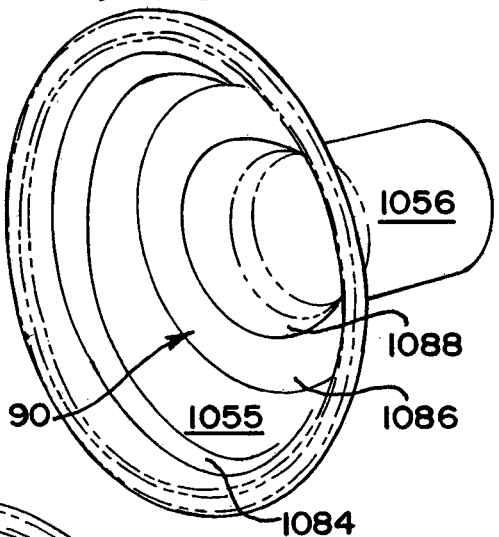
FIG. 26 is a perspective view of another adaptation of an inner shield part.

In FIG. 26, another variation on this same theme is presented, whereby ring projections are employed. These would include a ring 1084 in the conical part, a midrange ring 1086, and downstream of the midrange ring 1086 is the ring 1088, which begins at the forward end of the tubular part 1056. The rings 1084, 1086, 1088 may be either solid protrusions or presented as air chambers, or be a combination of both. When a vacuum source is applied to the space 1070 between the inner shield part and the outer shield part, the inner shield part will once again move in a longitudinal direction away from a woman's breast so that the rings (whether protruding (solid) or indented (chambers)) will cause a simultaneous massaging of the woman's breast and nipple received within the interior space 90. A cross-sectional representation of the conical parts in the vicinity of ring 1084 is shown in FIG. 24A.

Figure 27:
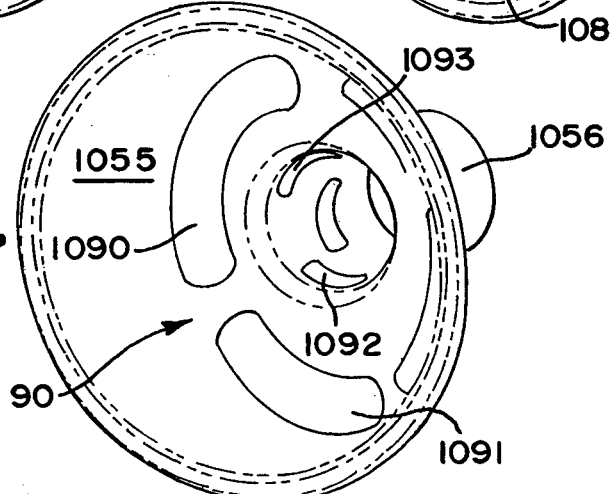
FIG. 27 is a perspective view of yet another adaptation of an inner shield part.

Still another variation of the embodiment of FIG. 26 is presented in FIG. 27, where a series of intermittent, or discontinuous, rings may be provided. These rings may also alternate as male and female segments, that is, one segment extending inboard, and another indented outboard. A male segment 1090 would present a protrusion, while the female segment 1091 would present a depression relative to the breast. The segments may become progressively smaller, as shown with segments 1092 and 1093.

Figure 28:
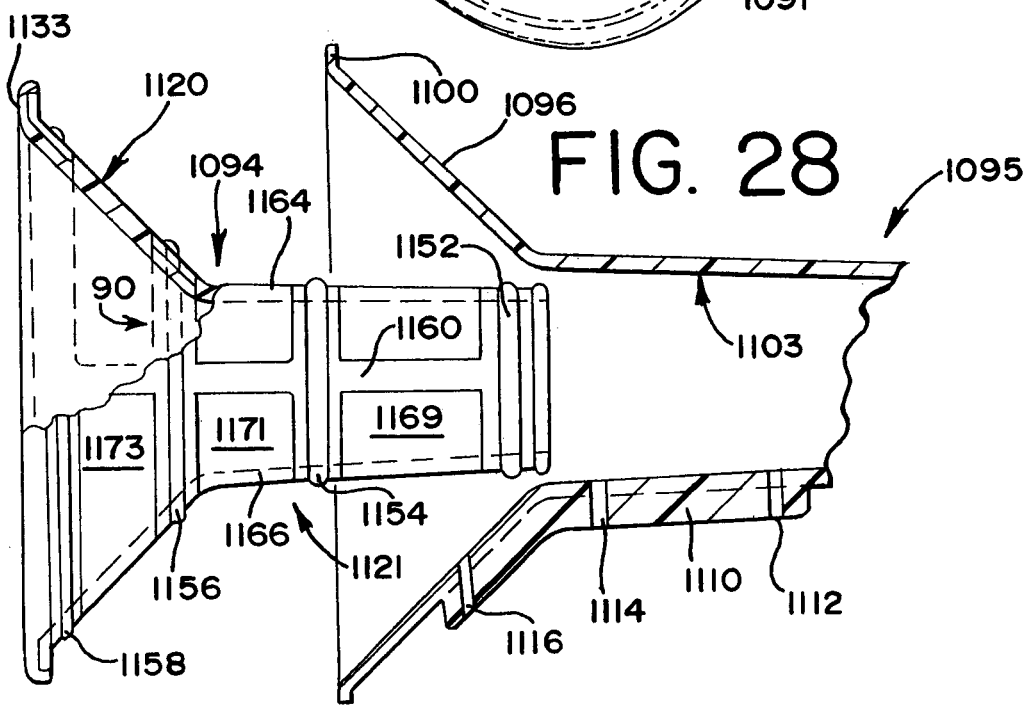
FIG. 28 is an exploded sectional view of an eighteenth embodiment of a breastshield constructed in accordance with an aspect of the present invention.
Figure 29:
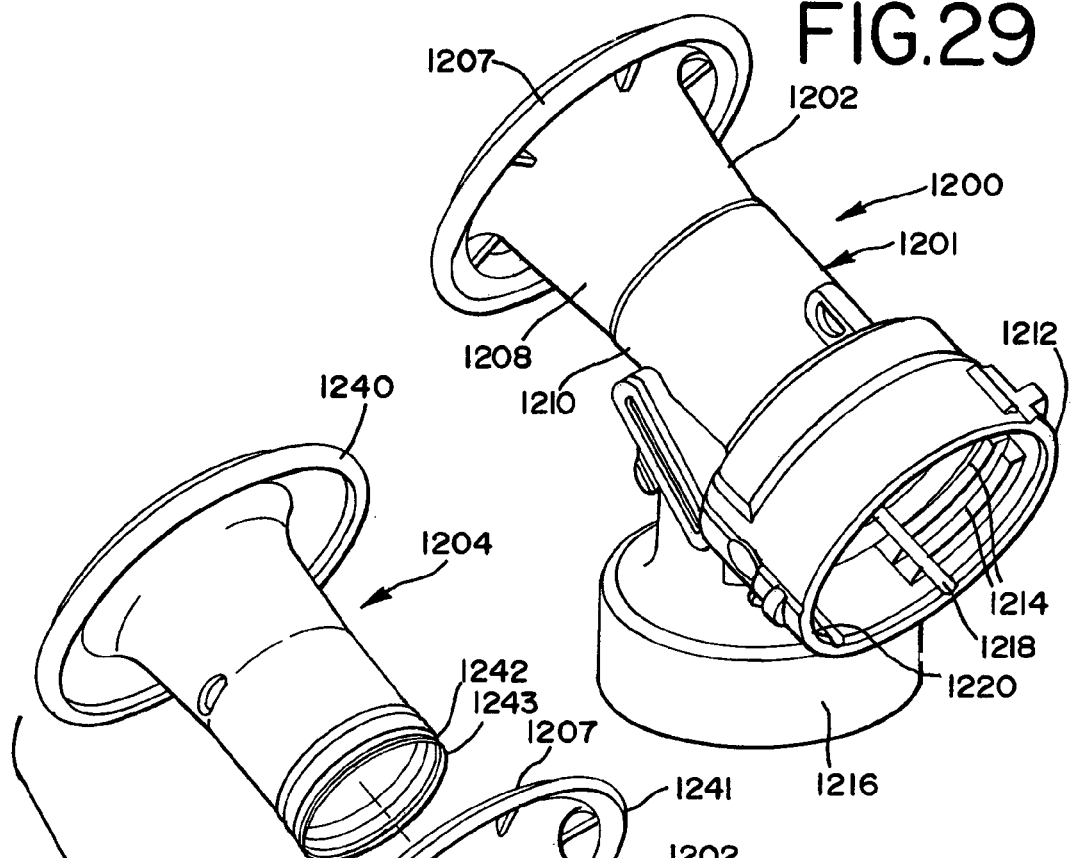
FIG. 29 is a perspective view of a nineteenth embodiment of a breastshield and additional related parts of a breastpump assembly constructed in accordance with an aspect of the present invention.
Figure 30:
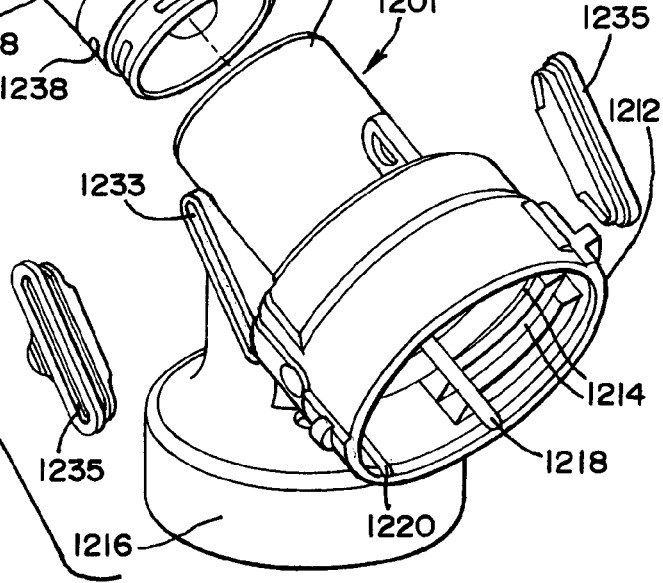
FIG. 30 is an exploded perspective view of the breastshield and related parts shown in FIG. 29.

In FIG. 28, an eighteenth embodiment of the present breastshield 1095 is presented. In this embodiment, the rigid outer shield part comprises a conical member 1096 with a forward rim or lip 1100, and a tubular portion 1103; the details of the downstream end of the rigid outer shield part are omitted, since any number of the foregoing embodiments can supply the same. A difference presented by this embodiment of FIG. 28 is the pressure manifold 1110 on one side of the outer shield part, which includes a first inlet port 1112, the second inlet port 1114, and the third inlet port 1116. The function of the inlet ports will be explained in greater detail shortly.

The breastshield 1095 of FIG. 28 also includes a flexible inner shield part 1094, which in this embodiment, is formed with a skeletal frame of thickened circumferential and longitudinal rib-like structures. The inner flexible shield part 1094 is comprised of a conical section 1120 integrally extending into tubular extension 1126. Each section 1120, 1126 is generally complementary in shape to the conical and cylindrical members 1096 and 1103 of the rigid outer shield part.

The skeletal frame is generally configured to engage with the interior sidewall of the outer shield part, and is comprised of a series of longitudinally spaced circumferential or perimetrical ribs 1152, 1154, 1156 and 1158, and stiffening longitudinally extending ribs 1160, 1164 and 1166.

When the flexible inner shield part 1094 is inserted within the rigid outer shield part, the rim 1133 of the flexible shield part 1094 engages around the rim 1100 to fix the inner shield part at this juncture. The spaced circumferential ribs 1152, 1154, 1156 and 1158 then form airtight seals against the internal wall surface of the sidewall defining the tubular portion 1103 of the rigid shield part. The space existing in-between the ribs form a plurality of separate pressure chambers 1169, 1171, and 1173. Each pressure chamber 1169, 1171, 1173 is respectively in fluid communication with the first, second, and third inlet ports 1112, 1114 and 1116 on the pressure manifold 1110. Thus, a positive pressure fluid source (not shown) provided to the pressure manifold 1110 will cause the inner flexible shield part that corresponds with each pressure chamber 1169, 1171 and 1173, to expand into the interior space 90 in a toroidal fashion similar to that of FIG. 20, for instance. A negative pressure fluid source (not shown) is provided to the interior space 90 in a known manner, so that the combination of suction on a breast received within interior space 90 and the positive pressure applied to a breast and nipple through the expanded formations, massage the breast and nipple simultaneously to facilitate milk expression. Alternatively, one can also pull vacuum through the pressure manifold 1110, thereby isolating the vacuum source from the breast in this manner. It will be noted that the stiffening longitudinal ribs 1160, 1164 and 1166 are radially lower in height than the circumferential ribs. The stiffening ribs serve to reduce the tendency of the flexible inner shield member to contract or expand along its longitudinal length.

Another embodiment is shown in FIGS. 29 through 34 (and 34A and 34B). This embodiment 1200 has a rigid outer shield part which is in two main pieces 1201, which is a base part, and 1202, which is the breast receptacle part. The flexible inner shield part is indicated at 1204.

A conical forward portion 1207 and slightly tapering tubular portion 1208 make up the breast receptacle piece 1202. This piece 1202 snap-engages with the base part 1201 at a complementary shaped tubular portion 1210 of the base piece 1201. The snap-engagement will be described hereafter. The base tubular portion 1210 which forms a mount for the downstream end of the receptacle tubular portion 1208 extends into a collar 1212, to which a manual pump may be attached, as through a screw-threaded engagement via threads 1214. An electrically-driven motorized pump may also be connected via tubes at the collar 1212, and this arrangement will be further described below. Base piece 1201 also has a collar 1216 for connection to a bottle, in the usual fashion.

Figure 31:
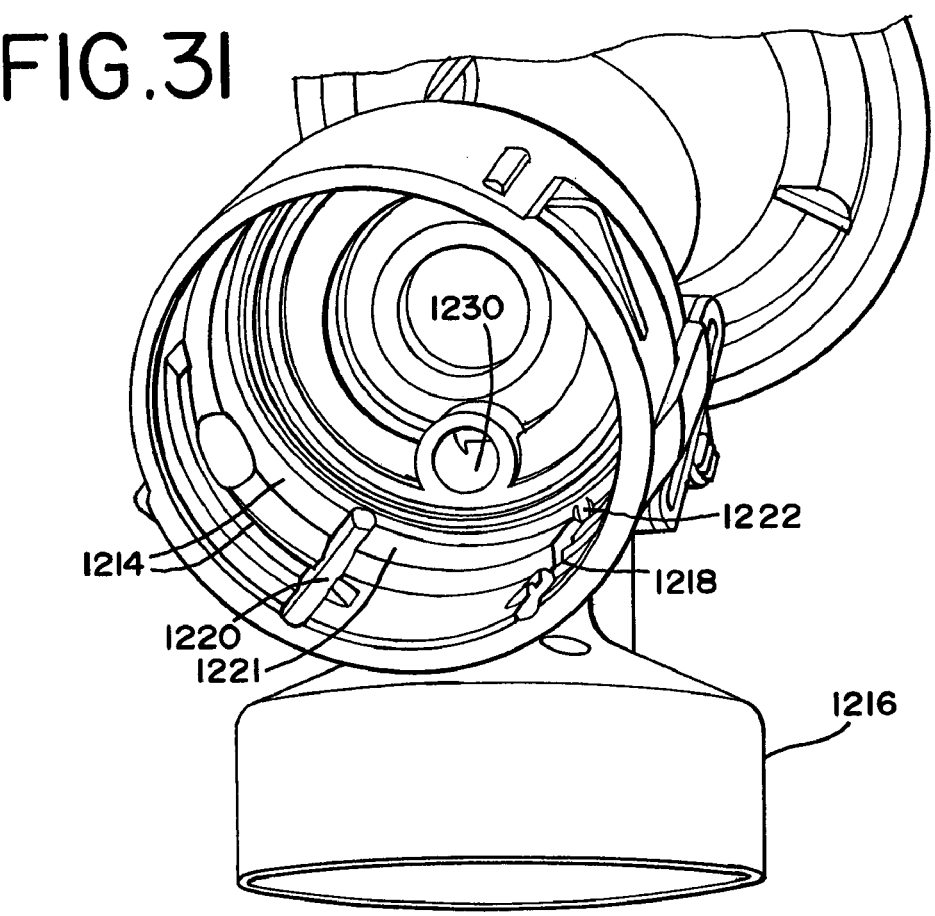
FIG. 31 is an enlarged-size rear perspective view of the breastshield and related parts shown in FIG. 29.

Base piece 1201 has first and second lateral ports 1218 and 1220 formed in the collar 1212. As seen in FIG. 31, for instance, these ports 1218 and 1220 start out as troughs or channels moving rearwardly to forwardly from the open send of the collar 1212, each terminating in a respective throughbore 1222, 1221 that extends within further structure of the base part, as will be described hereafter.

In addition to the ports 1218, 1220, is a port 1230 (FIG. 31). Port 1230 extends into the interior 90 (FIG. 32) of the breast receptacle, and will provide the principal negative (suction) pressure on the breast and nipple within the interior 90.

The ports 1218, 1220, via their respective throughbores 1221, 1222, each extend into a respective passageway or conduit formed in the base part 1201, which is indicated at 1233 for port/throughbore 1220/1221; a similar, although not depicted conduit is provided on the other side for port/throughbore 1218/1222. As a result of the molding process used for this particular embodiment, caps 1235 close the outboard sides of these conduits. The conduit 1233, like its counterpart, terminates in an interior outlet (not shown) through the sidewall defining the tubular part 1210.

The foregoing interior outlet aligns with a hole 1238 formed in the rearward end of the tubular part of the breast receptacle piece 1202, when the latter is mounted to the tubular portion 1210. That mounting is effected by placing the flexible inner shield part 1204 within and on the breast receptacle piece 1202 by inserting the former within the latter, with a beaded rim 1240 at the forward end of the flexible inner shield part snap-fitting over a flange or rim 1241 of the forward end of piece 1202. The rearward portion of the flexible shield part has a groove 1242 and terminal bead 1243 which, when folded back upon the flexible shield part (see FIGS. 30 and 32), are respectively received upon a bead 1244 and in a groove 1245 on the downstream end of the breast receptacle part 1202. This also serves to use the flexible shield part as a gasket in the interconnection of the rigid pieces 1202 and 1201.

Figure 32:
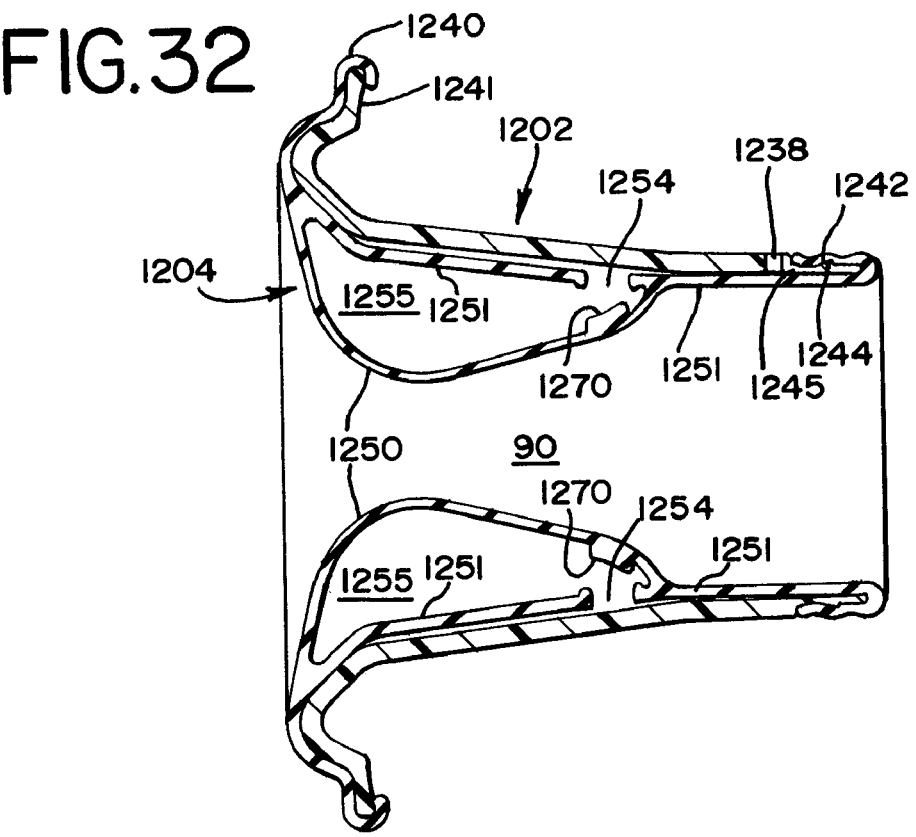
FIG. 32 is a sectional view of the breastshield of FIG. 29.

As shown in FIG. 32, the flexible shield part 1204 is made up of a double-walled structure having an interior sidewall 1250 and outboard sidewall 1251. One or more holes 1254 are provided in the outboard sidewall 1251, which communicate with the hole 1238 formed in the sidewall of the adjacent rigid part 1202. This double-walled structure yields a chamber 1255 in the flexible shield part 1204. Sidewall 1251 could be eliminated in a modified version.

Figure 34B:
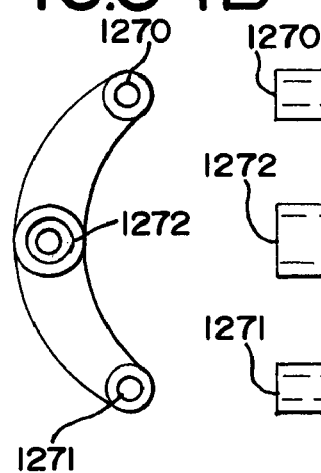
FIG. 34B is an end view from the other end of the adapter of FIG. 34.
Figure 34:
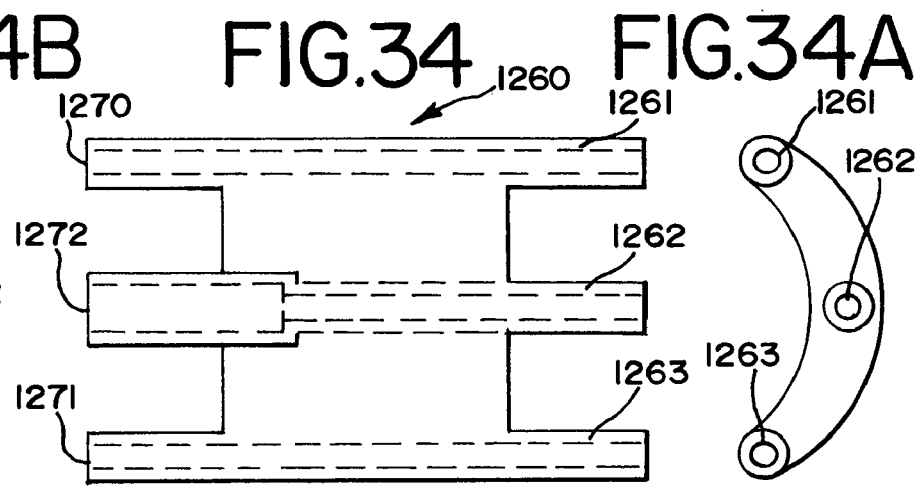
FIG. 34 is a top plan view of an adapter for air tubes for use with the breastshield and related parts shown in FIG. 29.
Figure 34A:
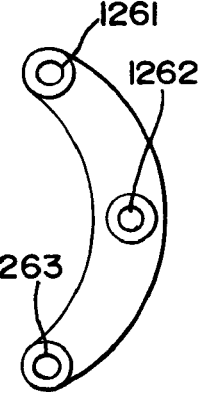
FIG. 34A is an end view from one end of the adapter of FIG. 34.
Figure 37:
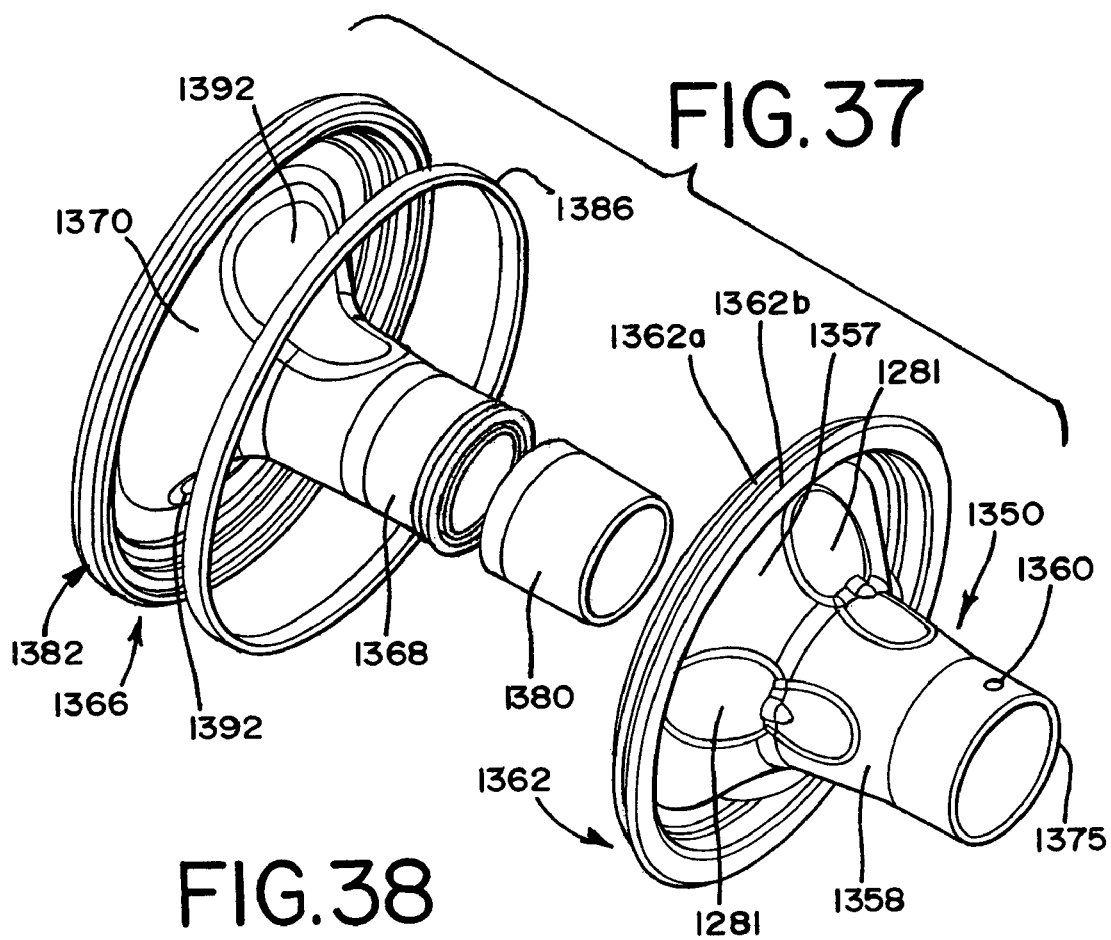
FIG. 37 is an exploded perspective view of a twenty-first embodiment of a breastshield made in accordance with the invention.
Figure 38:
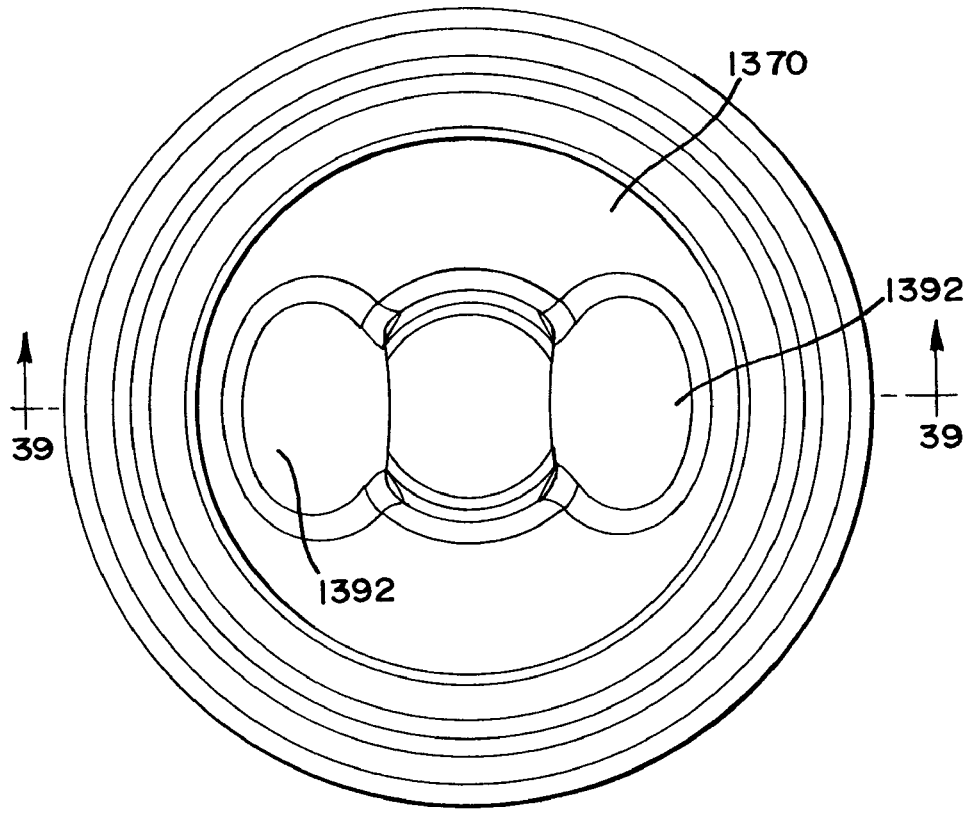
FIG. 38 is a side view in section of the assembled embodiment of FIG. 37.

Referring to FIGS. 34, 34A and 34B, there is shown a connector device 1260 for use in connecting pressure sources to the breastshield of this embodiment. The connector device comprises a structure having lateral passageways 1261 and 1263, with a central passageway 1262 defined therein. There are forward connectors sized to be received within the ports/throughbores 1218/1222, 1220/1221 and port 1230, indicated at 1270, 1271 and 1272 respectively. Nipples are formed on the opposite ends for connection with tubes to appropriate pressure sources.

With connector device 1260 in place within the collar 1212, pressure sources can be variously connected to the interior 90 and chamber 1255. For instance, a negative pressure source can be connected to each of the foregoing tube connections of the connector device 1260. This would result in the breast being pulled by suction into the interior 90. Simultaneously, for example, chamber 1255 can be reduced in volume, thereby drawing the sidewalls 1250 radially outwardly.

Integrally molded plugs 1270 are provided for use in manufacture, for purposes of permanently sealing the chamber 1255 after being filled with water, a gel, air, or the like. If a positive pressure were to be applied to inner chamber 1255, a rigid snap-ring would be advantageously used overlying rims 1240 and 1241.

Figure 33:
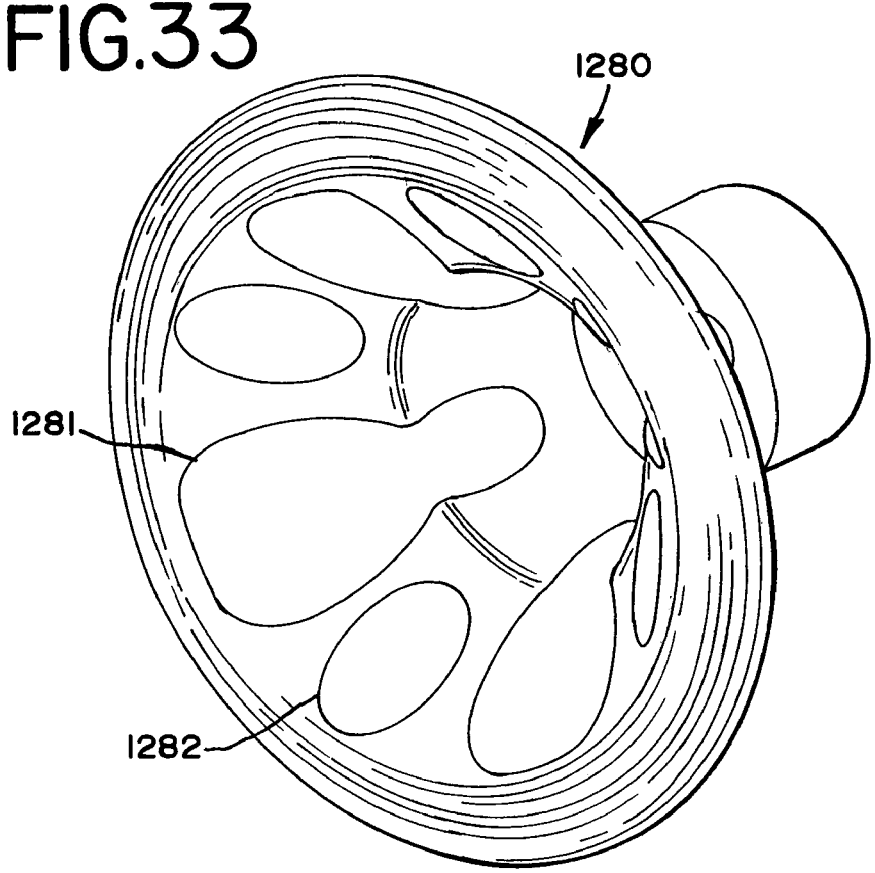
FIG. 33 is a perspective view of a modified breastshield of the type shown in FIG. 29.

FIG. 33 shows an alternative embodiment of the breast receptacle part 1202 of the preceding embodiment. This part 1280 is for all intents and purposes the same as that of part 1202, except that instead of one symmetrical internal sidewall 1250 presented to the breast, this version has a plurality of inboard opening concavities 1281, 1282. The flexible inner shield part can be pulled into these concavities under negative pressure applied outboard to the inner shield part.

FIGS. 35 and 36 illustrate yet another embodiment of the invention. This breastshield has a rigid outer shield part 1300 and flexible inner shield part 1302. The two shield parts 1300 and 1302 are molded as an integral unit. The flexible inner shield part 1302 begins at a point slightly in from the circumferential rim 1304 and extends into the tubular extension 1306 of the outer shield part 1300, where it relatively smoothly transitions into the wall of the extension.

There is a ring 1308 formed on the interior of the outer shield part 1300 upon which the flexible inner shield part 1300 overlies in this region. There are additional strut-like structures 1310 formed on the lateral sides of the outer shield part, which can add strength to the rigid shield, or simply perform some ornamentation. A spigot 1312 for connection of a hose from a pressure source is formed on the outer shield part 1302, and communicates with the interior of the rigid shield part.

A space 1318 is provided between the outboard side of the flexible inner shield part 1300 and the inboard side of the outer shield part 1302. This space 1318 is what is in communication with the spigot 1312.

Tubular extension 1306 has a tubular collar 1320 formed concentrically therein. That concentric arrangement yields a thin ring-shaped gap that tapers from a rearward opening toward a closed forward end. Into this gap is received the complimentary shaped tubular portion 1322 of a base part 1324. The tubular portion is received in an interference fit, and serves to mount the combined inner and outer shield parts to the base part. A downwardly depending apron 1330 from the outer shield part 1302 has a curvature to match that of a connecting length 1326 of the base part 1324, and serves to orient as well as stabilize the mounting. A rear wall 1334 is at the rearward side of the tubular portion 1322.

A port 1336 communicates vacuum from the pressure source, ultimately to the interior of the flexible inner shield part 1300. That vacuum passes from port 1336 through an internal channel 1338, which opens via outlet 1340 into the connecting length 1326. That length 1326 is closed by a flap valve structure (not shown), such that vacuum continues to travel past splash guard 1344 and up through inlets 1346 into the tubular portion 1322 of the base part 1324. Milk expressed into the tubular collar 1320 passes through the same inlets 1346 (now functioning as outlets, with inlets/outlets being relative terms in this context) into the connecting length 1326, and ultimately to a milk container.

A positive or negative pressure can be applied through spigot 1312. For one example, a negative pressure could be applied to the interior space 1318 simultaneously with the intermittent negative pressure (vacuum) to the interior 90 defined within the flexible inner shield part 1302 in a manner to initially prevent the flexible shield part 1302 from moving inboard under the influence of the interior vacuum that is pulling on the nipple/breast. That external vacuum (i.e., within space 1318) can then be released, and a positive pressure then applied to press the flexible shield part 1302 against and gently squeeze the breast at an advantageous stage in the expression sequence. This is but one way to apply differential pressures to the space 1318 and interior 90.

A twenty-first embodiment is illustrated in FIGS. 37 through 41. This embodiment has inner and outer shield parts similar to those discussed with respect to FIG. 33, with a base part similar to that described with relation to FIGS. 35 and 36. More particularly, outer rigid shield part 1350 has a conical forward portion 1357 which extends into a slightly tapering tubular portion 1358. Concavities 1281 as previously described are provided symmetrically around the longitudinal axis of the piece (that axis essentially being an axis of symmetry in this embodiment). A port 1360 extends through the sidewall of the tubular portion 1358, functioning in a manner as described with respect to port 1238 (e.g., FIG. 32).

The circumferential rim 1362 of the outer shield part is composed of two outboard extending flanges 1362a and 1362b, which are spaced apart in a vertical plane. These will engage the flexible inner shield part 1366 in a manner that will shortly be described.

Flexible inner shield part 1366, made of silicone or the like, is a single-walled structure having a shape which conforms to that of the funnel-shaped outer shield part 1350. It has a tubular extension portion 1368 which blends into a conical portion 1370. The tubular extension portion 1368 of the inner shield part 1366 has at its rearward (downstream) end a series of outboard extending circumferential ridges 1372 and 1373 which engage with the interior sidewall of the tubular portion 1358 when the inner shield and outer shield parts are mated (see, e.g., FIG. 41). Ridge 1373 overlies the rearward edge 1375 of the tubular portion 1358, and serves to position the inner shield part in place at this end. A rigid tubular (ring-shaped) sleeve or collar 1380 fits inside a two-piece region of the tubular extension portion 1368, the two-piece region being composed of sidewalls 1368a and 1368b. The sleeve 1380 is a stiffening element, to assure that the tubular portion 1368 stays firmly in place in use.

The conical portion 1370 has a circumferential rim 1382 which snap-fits over the rim 1362 of the outer shield part. An inboard circumferential extending bead 1382a is received in the gap between the rim elements 1362a and 1362b. Rim 1382 has a toroidal channel 1384 formed therein which receives a ring 1386 therein. Ring 1386 is a stiffening element to assure engagement of the outer and inner shield parts at this forward (upstream) end.

It will be noted that the inner shield part has a slightly inturned lip 1390 at its forwardmost end. This serves to prevent milk from spilling out of the breastshield, as when the breastshield is off the breast and tilted.

Flexible inner shield part 1366 further has protrusions 1392 formed on opposite sides thereof. These protrusions 1392 bow inwardly, i.e., into the interior 90 (thereby being concave outboardly). They are in the conical portion 1370 primarily, but also extend into the tubular extension 1368. When assembled with the outer shield part, the protrusions preferably overlie a set of the concavities 1281.

x In use, a positive pressure applied to the interior space between the inner and outer shield parts (via port 1360), serves to push the protrusions, as well as the flexible inner shield part above the sleeve 1380, inboard against the breast/nipple. A negative pressure (vacuum) pulls the protrusions as well as the inner shield part away, and if sufficient enough, into the concavities 1281. This is considered to enhance milk expression, providing a "feel" for the mother more reminiscent of a child's mouth, lips and tongue in suckling.

Thus, while a multitude of embodiments have been variously described herein, those of skill in this art will recognize that different embodiments show different potential features/designs which can be used in the other embodiments. Even more variations, applications and modifications will still fall within the spirit and scope of the invention, all as intended to come within the ambit and reach of the following claims.

What is claimed is:

1. A breastshield for a breastpump comprising:
a rigid outer shield part, said outer shield part having an internal funnel-shape with a widened upstream end extending into a tubular portion which terminates in a downstream end;
a flexible shield part, said flexible shield part having a shape generally conforming to and extending along the length of said internal funnel-shape and being received within said outer shield part, said flexible shield part having a longitudinal axis and an internal sidewall extending around said longitudinal axis and defining an interior to the breastshield and which is adapted to receive a nipple and at least some surrounding breast therein in a generally sealing engagement with said flexible shield part;
two or more projections positioned in said flexible shield part, at least one of said two or more projections being positioned at said tubular portion, each said two or more projections being in communication with a source of pressure and associated with an area of relatively weakened material of said flexible shield part, said two or more projections moving inwardly relative to said longitudinal axis upon application of a positive pressure between said projections and said rigid outer shield part; and
a fluid passageway communicating with said interior, whereby application of a source of negative pressure to said interior causes the breast to be pulled further into said interior and promotes the expression of breastmilk.

2. The breastshield of claim 1 wherein said two or more projections include a pair of projections positioned to expand at said tunnel part.

3. The breastshield of claim 2 wherein one of said two or more projections is positioned adjacent said widened upstream end.

* * * * *